US009688995B2

(12) United States Patent
Umemoto et al.

(10) Patent No.: US 9,688,995 B2
(45) Date of Patent: Jun. 27, 2017

(54) GENE ENCODING ENZYME THAT REDUCES POSITION 24 OF STEROID SKELETON AND PLANT IN WHICH EXPRESSION LEVEL OF THE GENE IS LOWERED

(71) Applicant: KIRIN HOLDINGS KABUSHIKI KAISHA, Nakano-ku, Tokyo (JP)

(72) Inventors: Naoyuki Umemoto, Nakano-ku (JP); Masako Otsuka, Nakano-ku (JP)

(73) Assignee: KIRIN HOLDINGS KABUSHIKI KAISHA, Tokyo (JP)

( * ) Notice: Subject to any disclaimer, the term of this patent is extended or adjusted under 35 U.S.C. 154(b) by 86 days.

(21) Appl. No.: 14/387,080

(22) PCT Filed: Mar. 22, 2013

(86) PCT No.: PCT/JP2013/058418
§ 371 (c)(1),
(2) Date: Sep. 22, 2014

(87) PCT Pub. No.: WO2013/141383
PCT Pub. Date: Sep. 26, 2013

(65) Prior Publication Data
US 2015/0052635 A1    Feb. 19, 2015

(30) Foreign Application Priority Data

Mar. 23, 2012  (JP) ................................ 2012-068039

(51) Int. Cl.
C12N 15/82   (2006.01)
A01H 1/00    (2006.01)
A01H 1/06    (2006.01)
C12Q 1/68    (2006.01)

(52) U.S. Cl.
CPC ........... *C12N 15/8216* (2013.01); *A01H 1/00* (2013.01); *A01H 1/06* (2013.01); *C12N 15/8245* (2013.01); *C12Q 1/6895* (2013.01); *C12Y 103/01072* (2013.01); *C12Q 2600/158* (2013.01)

(58) Field of Classification Search
None
See application file for complete search history.

(56) References Cited

U.S. PATENT DOCUMENTS

2012/0159676 A1    6/2012  Umemoto et al.

FOREIGN PATENT DOCUMENTS

| JP | 2012-239412 A | 12/2012 |
| WO | 2011/025011 A1 | 3/2011 |
| WO | 2012157677 A1 | 11/2012 |

OTHER PUBLICATIONS

Ding, B et al. The Plant Journal (1997) vol. 12, No. 4; pp. 931-936.*
Katsarou, K. et al. PLOS One (Mar. 3, 2016); pp. 1-17.*
Nahar, N Doctoral Thesis, Swedish University of Agricultural Sciences Uppsala 2011; Regulation of sterol and glycoalkaloid biosynthesis in potato (Solanum tuberosum L.)—Identification of key genes and enzymatic steps., pp. 1-66.*
Communication dated Sep. 15, 2015, issued by the Japan Patent Office in corresponding Japanese Application No. 2014-506305.
Nahar, "Regulation of sterol and glycoalkaloid biosynthesis in potato (Solanum tuberosum L.)—Identification of key genes and enzymatic steps", Doctoral Thesis, Swedish University of Agricultural Sciences, Acta Universitatis agriculturae Sueciae, 2011:15, URL, http://pub.epsilon.slu.se/2444/, 68 pages total.
Communication dated Nov. 2, 2015, from the European Patent Office in counterpart European Application No. 13764240.1.
Lisa Arnqvist: "Plant sterol metabolism with emphasis on glycoalkaloid biosynthesis in potato" In: 2007, Swedish University of Agricultural Sciences Uppsala, XP055220817, ISSN: 1652-6880 vol. 128.
Idit Ginzberg et al: "Introduction of potato steroidal glycoalkaloid biosynthetic pathway by overexpression of cDNA encoding primary metabolism HMG-CoA reductase and squalene synthase" , Planta; An International Journal of Plant Biology, Springer, Berlin, DE, (2012) vol. 235, No. 6: 1341-1353.
"Solanum tuberosum mRNA for sterol reductase (dwf1/DIMINUTO gene), clone cSTS3J19" GenBank, Aug. 2, 2010, Retrieved on May 22, 2013, http://www.ncbi.nlm.nih.gov/nuccore.FN995650.
Eckart Eich, "Solanaceae and Convolvulaceae: Secondary Metabolites", Biosynthesis, Chemotaxonomy, Biological and Economic Significance (A Handbook), 2008, pp. 398-461.
Idit Ginzberg et al., "Potato Steroidal Glycoalkaloids: Biosynthesis and Genetic Manipulation", Potato Research 2009, pp. 1-15, vol. 52.
Toshihiro Nohara et al., "The Tomato Saponin, Esculeoside A", J. Nat. Prod. 2010, pp. 1734-1741, vol. 73.
Kent F. McCue et al., "Metabolic compensation of steroidal glycoalkaloid biosynthesis in transgenic potato tubers: using reverse genetics to confirm the in vivo enzyme function of a steroidal alkaloid galactosyltransferase", Plant Science 2005, pp. 267-273, vol. 168.
Kent F. McCue et al., "The primary in vivo steroidal alkaloid glucosyltransferase from potato", Phytochemistry 2006, pp. 1590-1597, vol. 67.
Kent F. McCue et al., "Potato glycosterol rhamnosyltransferase, the terminal step in triose side-chain biosynthesis", Phytochemistry 2007, pp. 327-334, vol. 68.
Lisa Arnqvist et al., "Reduction of Cholesterol and Glycoalkaloid Levels in Transgenic Potato Plants by Overexpression of a Type 1 Sterol Methyltransferase cDNA", Plant Physiology 2003, pp. 1792-1799, vol. 131.
Sunghwa Choe et al., "The Arabidopsis *dwarf1* Mutant Is Defective in the Conversion of 24-Methylenecholesterol to Campesterol in Brassinosteroid Biosynthesis", Plant Physiology, Mar. 1999, pp. 897-907, vol. 119.

(Continued)

Primary Examiner — Russell Kallis
(74) Attorney, Agent, or Firm — Sughrue Mion, PLLC

(57) ABSTRACT

This invention provides a plant belonging to the family Solanaceae that does not produce cholesterols, including glycoalkaloids. This invention concerns a protein having activity of an enzyme that reduces position 24 of the steroid skeleton of a plant belonging to the family Solanaceae, a novel plant in which a gene encoding such protein is suppressed, and a method for producing and testing such plant.

8 Claims, 8 Drawing Sheets

(56) References Cited

OTHER PUBLICATIONS

Ulrich Klahre et al., "The Arabidopsis *DIMINUTO/DWARF1* Gene Encodes a Protein Involved in Steroid Synthesis", The Plant Cell, Oct. 1998, pp. 1677-1690, vol. 10.
Erich Heftmann, "Biogenesis of Steroids in Solanaceae", Phytochemistry 1983, pp. 1843-1860, vol. 22, No. 9.
Echart Eich, "Solanaceae and Colvolvulaceae: Secondary Metabolites" Biosynthesis, Chemotaxonomy, Biological and Economic Significance (A Handbook), 2008, pp. 368-373.
Ko Kaneko et al., "Structure of Barogenin From *Solanum tuberosum*", Phytochemistry 1977, pp. 791-793, vol. 16.

* cited by examiner

Fig. 1

1st amino acid sequence:StDWF1H
2nd amino acid sequence:StDWF1

```
  1' MSDAKAPAAA VHPRRKIQLV DFLLSFRWII VIFFVLPFSF LYYFSIYLGD LKSEKKSYKQ
      *,  .*.**  ...  *.*. ****. *** ***.**  *******.**  ..** *****
  1"      MTDVQAP PRPKRKKNIM DLLVQFRWIV VIFVVLPLSF LYYFSIYVGD VRSECKSYKQ

61' RQMEHDENVK EVVKRLEQRN AEKDGLVCTA RPPWVVVGMR NVDYKRARHF EVDLSKFRNI
     **.*******  .*****..** *.********  * ***.****  **********  ***** ***.
 58" RQKEHDENVK KVVKRLKDRN ASKDGLVCTA RKPWVAVGMR NVDYKRARHF EVDLSPFRNV

121' LDIDTERMVA KVEPLVNMGQ MSRVAIPMNL SLAVLAELDD LTVGGLINGF GVEGSSHIFG
      *. *******.*  **********  .***..***  ****.*****  **********.  *.*******.*
118" LNIDTERMIA KVEPLVNMGQ ISRVTVPMNV SLAVVAELDD LTVGGLINGY GIEGSSHIYG

181' LFSDTVVALE VVLADGKVVR ATKDNEYSDL FYAIPWSQGT LGLLVSAEIK LIPVDQYVKL
     *******.  *  ******.***  **********  **********  **********  ***...*.**
178" LFSDTVVSYE VVLADGQVVR ATKDNEYSDL FYAIPWSQGT LGLLVSAEIK LIPIKEYMKL

241' TYKPVRGNLQ ELAQAYADSF APKDGDQDNP SKVPEMVEGM IYGPTEGVMM TGMYASRNEA
     ***** ***. *.**** ***  .********,  .***..**.*  .*.***.* * ** **.***..**
238" TYKPVVGNLK EIAQAYIDSF SPKDGDQDNR EKVPDFVETM VYTPTEAVCM TGRYASKEEA

301' KRRGNVINNY GWWFKPWFYQ HAQTALKRGE FVEYIPTRDY YHRHTRSLYW EGKLILPFGD
     *,. ****** *****.**** *******.** ********.* *******.*** **********
298" KKKGNVINNV GWWFKTWFYQ HAQTALKKGE FVEYIPTREY YHRHTRCLYW EGKLILPFGD

361' QFWFRFLLGW LMPPKIALLK ATQSEAIRNY YHDHHVIQDL LVPLYKVGDC LEWVHREMEV
     *,.****,.** ****,,*** ***,* **** **..,*****,. ********* ****,*****
358" QWWFRFFFGW AMPPKVSLLK ATQGEYIRNY YHENHVIQDM LVPLYKVGDA LEWVNREMEV

421' YPIWLCPHRI YKLPVRPMIY PEPGFEKHKR QGDTEYAQMY TDIGVYYVPG AVLRGEPFDG
     **.******,. *,**..,*.* ****** *** ****.***** **.****.**  ..**** ***
418" YPLWLCPHRL YRLPLKTMVY PEPGFELHKR QGDTKYAQMY TDVGVYYAPG PILRGEVFDG

481' SEKCRQLELW LIENHGFDAQ YAVTELTEKN FWRMFDNSLY EQCRRKYKAI GTFMSVYYKS
     * *.** * ********.* ***.****** ******.*** *.**.**.** **********
478" IEAVRKLESW LIENHGFQPQ YAVSELTEKN FWRMFDGSLY ENCRKKYRAI GTFMSVYYKS

541' KKGRKTEKEV QEAEQEKAEQ ETPEADEPAN (SEQ ID NO: 1)
     ***.****** *,****.** ****.***..
538" KKGKKTEKEV QDAEQETAEV ETPEVDEPED (SEQ ID NO: 5)
```

1  2  3  4  5  6  7

1: Non-transformant
2: Non-transformant
3: pKT251 transformant #2
4: pKT250 transformant #10
5: pKT250 transformant #11
6: pKT250 transformant #12
7: pKT250 transformant #9

SEQUENCE LISTING

<160> NUMBER OF SEQ ID NOS: 22

<210> SEQ ID NO 1
<211> LENGTH: 570
<212> TYPE: PRT
<213> ORGANISM: Solanum tuberosum

<400> SEQUENCE: 1

Met Ser Asp Ala Lys Ala Pro Ala Ala Val His Pro Arg Lys
1               5                   10                  15

Ile Gln Leu Val Asp Phe Leu Leu Ser Phe Arg Trp Ile Ile Val Ile
                20                  25                  30

Phe Phe Val Leu Pro Phe Ser Phe Leu Tyr Tyr Phe Ser Ile Tyr Leu
            35                  40                  45

Gly Asp Leu Lys Ser Glu Lys Lys Ser Tyr Lys Gln Arg Gln Met Glu
        50                  55                  60

His Asp Glu Asn Val Lys Glu Val Val Lys Arg Leu Glu Gln Arg Asn
65                  70                  75                  80

Ala Glu Lys Asp Gly Leu Val Cys Thr Ala Arg Pro Pro Trp Val Val
                85                  90                  95

Val Gly Met Arg Asn Val Asp Tyr Lys Arg Ala Arg His Phe Glu Val
            100                 105                 110

Asp Leu Ser Lys Phe Arg Asn Ile Leu Asp Ile Asp Thr Glu Arg Met
        115                 120                 125

Val Ala Lys Val Glu Pro Leu Val Asn Met Gly Gln Met Ser Arg Val
    130                 135                 140

Ala Ile Pro Met Asn Leu Ser Leu Ala Val Leu Ala Glu Leu Asp Asp
145                 150                 155                 160

Leu Thr Val Gly Gly Leu Ile Asn Gly Phe Gly Val Glu Gly Ser Ser

```
                        165                 170                 175
His Ile Phe Gly Leu Phe Ser Asp Thr Val Ala Leu Glu Val Val
                180                 185                 190
Leu Ala Asp Gly Lys Val Val Arg Ala Thr Lys Asp Asn Glu Tyr Ser
            195                 200                 205
Asp Leu Phe Tyr Ala Ile Pro Trp Ser Gln Gly Thr Leu Gly Leu Leu
        210                 215                 220
Val Ser Ala Glu Ile Lys Leu Ile Pro Val Asp Gln Tyr Val Lys Leu
225                 230                 235                 240
Thr Tyr Lys Pro Val Arg Gly Asn Leu Gln Glu Leu Ala Gln Ala Tyr
                245                 250                 255
Ala Asp Ser Phe Ala Pro Lys Asp Gly Asp Gln Asp Asn Pro Ser Lys
            260                 265                 270
Val Pro Glu Met Val Glu Gly Met Ile Tyr Gly Pro Thr Glu Gly Val
        275                 280                 285
Met Met Thr Gly Met Tyr Ala Ser Arg Asn Glu Ala Lys Arg Arg Gly
290                 295                 300
Asn Val Ile Asn Asn Tyr Gly Trp Trp Phe Lys Pro Trp Phe Tyr Gln
305                 310                 315                 320
His Ala Gln Thr Ala Leu Lys Arg Gly Glu Phe Val Glu Tyr Ile Pro
                325                 330                 335
Thr Arg Asp Tyr Tyr His Arg His Thr Arg Ser Leu Tyr Trp Glu Gly
            340                 345                 350
Lys Leu Ile Leu Pro Phe Gly Asp Gln Phe Trp Phe Arg Phe Leu Leu
        355                 360                 365
Gly Trp Leu Met Pro Pro Lys Ile Ala Leu Leu Lys Ala Thr Gln Ser
        370                 375                 380
Glu Ala Ile Arg Asn Tyr Tyr His Asp His His Val Ile Gln Asp Leu
385                 390                 395                 400
Leu Val Pro Leu Tyr Lys Val Gly Asp Cys Leu Glu Trp Val His Arg
                405                 410                 415
Glu Met Glu Val Tyr Pro Ile Trp Leu Cys Pro His Arg Ile Tyr Lys
            420                 425                 430
Leu Pro Val Arg Pro Met Ile Tyr Pro Glu Pro Gly Phe Glu Lys His
        435                 440                 445
Lys Arg Gln Gly Asp Thr Glu Tyr Ala Gln Met Tyr Thr Asp Ile Gly
        450                 455                 460
Val Tyr Tyr Val Pro Gly Ala Val Leu Arg Gly Glu Pro Phe Asp Gly
465                 470                 475                 480
Ser Glu Lys Cys Arg Gln Leu Glu Leu Trp Leu Ile Glu Asn His Gly
                485                 490                 495
Phe Gln Ala Gln Tyr Ala Val Thr Glu Leu Thr Glu Lys Asn Phe Trp
            500                 505                 510
Arg Met Phe Asp Asn Ser Leu Tyr Glu Gln Cys Arg Arg Lys Tyr Lys
        515                 520                 525
Ala Ile Gly Thr Phe Met Ser Val Tyr Tyr Lys Ser Lys Lys Gly Arg
        530                 535                 540
Lys Thr Glu Lys Glu Val Gln Glu Ala Glu Gln Glu Lys Ala Glu Gln
545                 550                 555                 560
Glu Thr Pro Glu Ala Asp Glu Pro Ala Asn
                565                 570

<210> SEQ ID NO 2
```

<211> LENGTH: 1710
<212> TYPE: DNA
<213> ORGANISM: Solanum tuberosum

<400> SEQUENCE: 2

```
atgtcggatg ctaaggcccc cgcggccgcc gttcacccta ggaggaagat ccagttggtg      60
gactttcttc tttcgttccg atggatcatt gttatctttt ttgtccttcc attctcgttc     120
ttgtattact tctccatata tctaggggat ttgaagtctg agaagaaatc ttacaagcaa     180
cgccagatgg aacacgatga gaatgttaaa gaggttgtga agcgccttga acagaggaat     240
gcagaaaagg atggtcttgt ctgcacggcc aggcctcctt gggttgttgt tggaatgaga     300
aacgtagact ataaacgtgc tcgtcatttt gaagttgatc tttctaagtt tagaaatata     360
cttgatattg acacggaacg tatggttgcc aaagttgagc ctcttgtcaa tatgggccaa     420
atgtcaaggg tcgccatccc aatgaatctt tcccttgcag ttcttgctga gcttgatgat     480
cttaccgttg gaggtttgat caatgggttc ggggtcgaag gaagttctca catctttgga     540
ttgttctctg acactgttgt agcacttgag gttgttctag ctgatggaaa ggttgttaga     600
gctacaaagg acaacgaata ttctgatctt ttctacgcta ttccgtggtc tcaagggaca     660
ttggggcttc ttgtttcagc tgaaatcaag cttataccag ttgatcaata cgtaaaactt     720
acctacaaac ctgtaagggg taatcttcaa gagcttgcac aggcttacgc ggattctttt     780
gcacctaaag atggagatca ggacaatcct tctaaagttc cagagatggt agaaggcatg     840
atttatggtc aacagaagg tgttatgatg accggtatgt atgcttcgag gaatgaagcc     900
aaacgaaggg gtaatgtaat caacaattat ggttggtggt tcaaaccatg gttttaccaa     960
cacgctcaaa ccgcactgaa agaggggaa tttgtggagt acatcccaac tagggactac    1020
taccacaggc acacgagatc gttgtattgg gaagggaaac taattcttcc atttggtgat    1080
cagttctggt ttaggttcct cttaggatgg ctcatgccac caaagattgc tctgctcaaa    1140
gccacacaaa gtgaggctat tagaaactat accatgacc atcatgtcat tcaggatctg    1200
cttgttcctc tttacaaggt cggcgattgt ctcgagtggg ttcaccgcga gatggaggta    1260
tatcccattt ggctctgccc acacagaatt acaagctgc ctgtgagacc tatgatctac    1320
cctgaaccag gattcgagaa acacaaaagg cagggtgaca ccgaatatgc acaaatgtac    1380
actgatattg tgtctactag tgttcccgga gcagtcctga ggggtgagcc atttgatgga    1440
tcagagaaat gccgccaact tgagctttgg ttgattgaaa accatggatt tcaggctcaa    1500
tacgcggtga ctgagctgac agagaagaat ttctggagga tgtttgataa cagtctgtac    1560
gagcaatgca gaaggaagta caaagctatt ggaacgttca tgagtgtgta ctataaatcg    1620
aagaaaggaa ggaagacaga gaaggaagtg caggaagctg agcaagagaa agctgaacaa    1680
gagactcctg aagctgatga acctgcgaat                                     1710
```

<210> SEQ ID NO 3
<211> LENGTH: 566
<212> TYPE: PRT
<213> ORGANISM: Solanum lycopersicum

<400> SEQUENCE: 3

```
Met Ser Asp Ala Lys Ala Pro Val Ala Thr Ala Tyr Pro Lys Arg Lys
 1               5                  10                  15

Ile Gln Leu Val Asp Phe Leu Leu Ser Phe Arg Trp Ile Ile Val Ile
            20                  25                  30

Phe Phe Val Leu Pro Phe Ser Phe Leu Tyr Tyr Phe Ser Ile Tyr Leu
```

```
                35                  40                  45
Gly Asp Val Lys Ser Glu Arg Lys Ser Tyr Lys Gln Arg Gln Met Glu
             50                  55                  60
His Asp Glu Asn Val Lys Glu Val Val Lys Arg Leu Gly Gln Arg Asn
 65                  70                  75                  80
Ala Glu Lys Asp Gly Leu Val Cys Thr Ala Arg Pro Pro Trp Val Val
                 85                  90                  95
Val Gly Met Arg Asn Val Asp Tyr Lys Arg Ala Arg His Phe Glu Val
                100                 105                 110
Asp Leu Ser Lys Phe Arg Asn Ile Leu Asp Ile Asp Thr Glu Arg Met
                115                 120                 125
Val Ala Lys Val Glu Pro Leu Val Asn Met Gly Gln Met Ser Arg Val
                130                 135                 140
Thr Ile Pro Met Asn Leu Ser Leu Ala Val Leu Ala Glu Leu Asp Asp
145                 150                 155                 160
Leu Thr Val Gly Gly Leu Ile Asn Gly Phe Gly Val Glu Gly Ser Ser
                165                 170                 175
His Ile Phe Gly Leu Phe Ser Asp Thr Val Val Ala Leu Glu Val Val
                180                 185                 190
Leu Ala Asp Gly Lys Val Val Arg Ala Thr Lys Asp Asn Glu Tyr Ser
                195                 200                 205
Asp Leu Phe Tyr Ala Ile Pro Trp Ser Gln Gly Thr Leu Gly Leu Leu
                210                 215                 220
Val Ser Ala Glu Ile Lys Leu Ile Pro Val Asp Gln Tyr Val Lys Leu
225                 230                 235                 240
Thr Tyr Lys Pro Val Arg Gly Asn Leu Lys Glu Leu Ala Gln Ala Tyr
                245                 250                 255
Ala Asp Ser Phe Ala Pro Lys Asp Gly Asp Gln Asp Asn Pro Ser Lys
                260                 265                 270
Val Pro Glu Met Val Glu Gly Met Ile Tyr Gly Pro Thr Glu Gly Val
                275                 280                 285
Met Met Thr Gly Met Tyr Ala Ser Arg Asn Glu Ala Lys Arg Arg Gly
                290                 295                 300
Asn Val Ile Asn Asn Tyr Gly Trp Trp Phe Lys Pro Trp Phe Tyr Gln
305                 310                 315                 320
His Ala Gln Thr Ala Leu Lys Arg Gly Glu Phe Val Glu Tyr Ile Pro
                325                 330                 335
Thr Arg Asp Tyr Tyr His Arg His Thr Arg Ser Leu Tyr Trp Glu Gly
                340                 345                 350
Lys Leu Ile Leu Pro Phe Gly Asp Gln Phe Trp Phe Arg Phe Leu Leu
                355                 360                 365
Gly Trp Leu Met Pro Pro Lys Ile Ala Leu Leu Lys Ala Thr Gln Ser
                370                 375                 380
Glu Ala Ile Arg Asn Tyr Tyr His Asp His His Val Ile Gln Asp Leu
385                 390                 395                 400
Leu Val Pro Leu Tyr Lys Val Gly Asp Cys Leu Glu Trp Val His Arg
                405                 410                 415
Glu Met Glu Val Tyr Pro Ile Trp Leu Cys Pro His Arg Ile Tyr Lys
                420                 425                 430
Leu Pro Val Arg Pro Met Ile Tyr Pro Glu Pro Gly Phe Glu Lys His
                435                 440                 445
Lys Arg Gln Gly Asp Thr Glu Tyr Ala Gln Met Tyr Thr Asp Val Gly
                450                 455                 460
```

```
Val Tyr Tyr Val Pro Gly Ala Val Leu Arg Gly Glu Pro Phe Asp Gly
465                 470                 475                 480

Ser Glu Lys Cys Arg Gln Leu Glu Leu Trp Leu Ile Glu Asn His Gly
                485                 490                 495

Phe Gln Ala Gln Tyr Ala Val Thr Glu Leu Thr Glu Lys Asn Phe Trp
            500                 505                 510

Arg Met Phe Asp Asn Gly Leu Tyr Glu Gln Cys Arg Arg Lys Tyr Lys
        515                 520                 525

Ala Ile Gly Thr Phe Met Ser Val Tyr Tyr Lys Ser Lys Lys Gly Arg
    530                 535                 540

Lys Thr Glu Lys Glu Val Gln Glu Ala Glu Gln Glu Lys Ala Glu Gln
545                 550                 555                 560

Glu Thr Pro Glu Ala Asn
                565

<210> SEQ ID NO 4
<211> LENGTH: 1698
<212> TYPE: DNA
<213> ORGANISM: Solanum lycopersicum

<400> SEQUENCE: 4
```

| | | | | | |
|---|---|---|---|---|---|
| atgtcggatg | ctaaggcccc | cgtggccact | gcttaccctg | agaggaagat | ccagttggtg | 60 |
| gacttccttc | tttcgttccg | atggatcatt | gtcatctttt | ttgtccttcc | attctcgttc | 120 |
| ttgtattact | tctcgatata | tctaggggat | gtgaaatccg | agaggaaatc | ttacaagcaa | 180 |
| cgccagatgg | aacacgatga | aatgttaaa | gaggttgtga | agcgtcttgg | ccagaggaat | 240 |
| gcagaaaagg | atggtcttgt | atgcacagcc | agacctcctt | gggtggttgt | tggaatgaga | 300 |
| aatgtcgact | ataaacgtgc | tcgtcatttt | gaagttgatc | tttcaaagtt | tagaaatata | 360 |
| cttgatattg | acacggagcg | gatggttgct | aaagttgagc | tctagtcaa | tatgggccaa | 420 |
| atgtcaaggg | tcactatccc | aatgaatctt | tcccttgcag | ttctcgctga | gctcgatgat | 480 |
| cttaccgttg | gtggtttgat | caatgggttc | ggggttgaag | aagttctca | catatttggg | 540 |
| ttgttctctg | cactgttgt | agcacttgag | gttgttctag | ctgatggaaa | ggttgttaga | 600 |
| gctacaaagg | acaacgaata | ttctgatctt | ttctacgcta | ttccgtggtc | tcaaggaaca | 660 |
| ttggggcttc | ttgtttcagc | tgaaatcaag | cttataccag | ttgatcaata | cgtgaaactt | 720 |
| acctacaaac | ctgtaagggg | taatcttaaa | gagcttgctc | aggcttacgc | ggattctttt | 780 |
| gcacctaaag | atggagatca | ggacaatcct | tctaaagttc | ctgagatggt | agaaggcatg | 840 |
| atttatggtc | caaccgaagg | ggttatgatg | accggtatgt | atgcttcgag | gaatgaagcc | 900 |
| aaacgaaggg | gtaatgtaat | caacaattac | ggttggtggt | tcaaaccatg | gttttaccaa | 960 |
| cacgctcaaa | ccgcactaaa | aagaggggaa | tttgttgagt | acattccaac | tagggactac | 1020 |
| taccacagac | acacgagatc | gttgtattgg | gaaggtaaac | taattcttcc | attcggtgat | 1080 |
| cagttctggt | ttaggttcct | cttaggatgg | ctcatgccac | caaagattgc | tctgctcaaa | 1140 |
| gccacacaaa | gtgaggctat | agaaactat | taccatgacc | atcatgtcat | tcaagatctc | 1200 |
| cttgttcctc | tttacaaggt | cggtgattgt | ctcgagtggg | ttcatcgcga | gatgcaggta | 1260 |
| tatccaattt | ggctgtgccc | acacagaatt | tacaagctgc | cagtgagacc | aatgatctac | 1320 |
| cctgaaccag | gattcgagaa | acacaaaagg | cagggtgaca | ccgaatatgc | acaaatgtat | 1380 |
| actgatgttg | gtgtgtacta | tgttccggga | gcagtcctga | ggggtgagcc | gtttgatggt | 1440 |
| tcagagaaat | gccgacaact | tgagctttgg | ttgatagaga | accatggatt | tcaggctcaa | 1500 |

```
tacgcggtga ctgagctgac agagaagaat ttctggagga tgtttgataa cggtctgtac    1560
gagcaatgca aaggaagta caaagctatc ggaacgttca tgagtgtgta ctataaatcg    1620
aagaaaggaa ggaagacaga gaaggaagtg caggaagctg agcaagagaa agctgaacaa    1680
gagactcctg aagcaaat                                                  1698

<210> SEQ ID NO 5
<211> LENGTH: 567
<212> TYPE: PRT
<213> ORGANISM: Solanum tuberosum

<400> SEQUENCE: 5

Met Thr Asp Val Gln Ala Pro Pro Arg Pro Lys Arg Lys Lys Asn Ile
1               5                   10                  15

Met Asp Leu Leu Val Gln Phe Arg Trp Ile Val Val Ile Phe Val Val
            20                  25                  30

Leu Pro Leu Ser Phe Leu Tyr Tyr Phe Ser Ile Tyr Val Gly Asp Val
        35                  40                  45

Arg Ser Glu Cys Lys Ser Tyr Lys Gln Arg Gln Lys Glu His Asp Glu
    50                  55                  60

Asn Val Lys Lys Val Val Lys Arg Leu Lys Asp Arg Asn Ala Ser Lys
65                  70                  75                  80

Asp Gly Leu Val Cys Thr Ala Arg Lys Pro Trp Val Ala Val Gly Met
                85                  90                  95

Arg Asn Val Asp Tyr Lys Arg Ala Arg His Phe Glu Val Asp Leu Ser
            100                 105                 110

Pro Phe Arg Asn Val Leu Asn Ile Asp Thr Glu Arg Met Ile Ala Lys
        115                 120                 125

Val Glu Pro Leu Val Asn Met Gly Gln Ile Ser Arg Val Thr Val Pro
    130                 135                 140

Met Asn Val Ser Leu Ala Val Val Ala Glu Leu Asp Asp Leu Thr Val
145                 150                 155                 160

Gly Gly Leu Ile Asn Gly Tyr Gly Ile Glu Gly Ser Ser His Ile Tyr
                165                 170                 175

Gly Leu Phe Ser Asp Thr Val Val Ser Tyr Glu Val Val Leu Ala Asp
            180                 185                 190

Gly Gln Val Val Arg Ala Thr Lys Asp Asn Glu Tyr Ser Asp Leu Phe
        195                 200                 205

Tyr Ala Ile Pro Trp Ser Gln Gly Thr Leu Gly Leu Leu Val Ser Ala
    210                 215                 220

Glu Ile Lys Leu Ile Pro Ile Lys Glu Tyr Met Lys Leu Thr Tyr Lys
225                 230                 235                 240

Pro Val Val Gly Asn Leu Lys Glu Ile Ala Gln Ala Tyr Ile Asp Ser
                245                 250                 255

Phe Ser Pro Lys Asp Gly Asp Gln Asp Asn Arg Glu Lys Val Pro Asp
            260                 265                 270

Phe Val Glu Thr Met Val Tyr Thr Pro Thr Glu Ala Val Cys Met Thr
        275                 280                 285

Gly Arg Tyr Ala Ser Lys Glu Glu Ala Lys Lys Gly Asn Val Ile
    290                 295                 300

Asn Asn Val Gly Trp Trp Phe Lys Thr Trp Phe Tyr Gln His Ala Gln
305                 310                 315                 320

Thr Ala Leu Lys Lys Gly Glu Phe Val Glu Tyr Ile Pro Thr Arg Glu
                325                 330                 335
```

```
Tyr Tyr His Arg His Thr Arg Cys Leu Tyr Trp Glu Gly Lys Leu Ile
            340                 345                 350

Leu Pro Phe Gly Asp Gln Trp Trp Phe Arg Phe Phe Gly Trp Ala
        355                 360                 365

Met Pro Pro Lys Val Ser Leu Leu Lys Ala Thr Gln Gly Glu Tyr Ile
370                 375                 380

Arg Asn Tyr Tyr His Glu Asn His Val Ile Gln Asp Met Leu Val Pro
385                 390                 395                 400

Leu Tyr Lys Val Gly Asp Ala Leu Glu Trp Val Asn Arg Glu Met Glu
            405                 410                 415

Val Tyr Pro Leu Trp Leu Cys Pro His Arg Leu Tyr Arg Leu Pro Leu
        420                 425                 430

Lys Thr Met Val Tyr Pro Glu Pro Gly Phe Glu Leu His Lys Arg Gln
        435                 440                 445

Gly Asp Thr Lys Tyr Ala Gln Met Tyr Thr Asp Val Gly Val Tyr Tyr
        450                 455                 460

Ala Pro Gly Pro Ile Leu Arg Gly Glu Val Phe Asp Gly Ile Glu Ala
465                 470                 475                 480

Val Arg Lys Leu Glu Ser Trp Leu Ile Glu Asn His Gly Phe Gln Pro
            485                 490                 495

Gln Tyr Ala Val Ser Glu Leu Thr Glu Lys Asn Phe Trp Arg Met Phe
        500                 505                 510

Asp Gly Ser Leu Tyr Glu Asn Cys Arg Lys Lys Tyr Arg Ala Ile Gly
            515                 520                 525

Thr Phe Met Ser Val Tyr Tyr Lys Ser Lys Lys Gly Lys Lys Thr Glu
        530                 535                 540

Lys Glu Val Gln Asp Ala Glu Gln Glu Thr Ala Glu Val Glu Thr Pro
545                 550                 555                 560

Glu Val Asp Glu Pro Glu Asp
            565

<210> SEQ ID NO 6
<211> LENGTH: 1704
<212> TYPE: DNA
<213> ORGANISM: Solanum tuberosum

<400> SEQUENCE: 6
atgacagatg ttcaggctcc ccctcgccct aagaggaaga aaaacattat ggaccttctt      60
gtccagttca gatggatcgt cgttatcttc gtcgtcctcc ctctctcttt cctgtattat     120
ttctctatat atgttgggga tgttagatct gagtgcaaat catacaagca gcgccagaag     180
gagcatgatg aaaatgttaa aaaggttgtg aagcgtctta aggataggaa tgcatctaag     240
gatggtcttg tctgcacagc tagaaagccc tgggttgctg ttggaatgag aaatgtggac     300
tacaagcgtg ctcgtcattt tgaagttgat ctttctccat ttagaaatgt tcttaacatt     360
gacacggagc gaatgattgc taaagtcgag cctctagtca atatgggcca aatctctaga     420
gttactgtcc ctatgaatgt tccctcgca gttgttgctg agcttgatga tctaactgtt      480
ggtggtctga tcaacggcta tgggattgaa ggaagttctc acatttatgg actgttctca     540
gacactgttg tgtcatatga agttgttcta gcagacgggc aggtagttag agctacaaag     600
gacaatgaat attctgatct tttctatgct attccatggt ctcaagggac tctgggcttt     660
ctggtttcag ctgagatcaa gctcattcca atcaaggaat acatgaaact tacctacaaa     720
cctgtagttg gtaatttgaa agagattgct caggcttata tagattcttt ttcacctaaa     780
```

```
gatgggatc aggataaccg tgagaaagtt ccggactttg tagaaaccat ggtgtacact      840
cccacagaag ctgtttgcat gactggtaga tatgcttcaa agaagaggc caagaagaag      900 ggcaatgtga tcaacaatgt tggttggtgg ttcaaaacct ggttttacca gcacgctcaa     960
actgcactca agaaggggga attcgtagag tacattccaa ctagggaata ctaccacagg    1020
cacacaagat gcttgtattg ggaagggaaa cttatccttc cattcggtga tcagtggtgg    1080
tttaggtttt tctttggatg ggccatgcct cccaaggttt ctctacttaa agccactcaa    1140
ggtgaataca ttaggaacta ttaccatgaa aaccatgtca ttcaggatat gcttgttcct    1200
ctttacaagg ttggcgatgc tcttgagtgg gtcaaccgtg agatggaggt gtatcccctc    1260
tggctctgcc cccacagact ctacaggctg cctcttaaaa caatggtgta ccctgaacca    1320
ggttttgagc tgcacaagag gcagggtgac acaaaatatg ctcaaatgta caccgatgtt    1380
ggtgtctact atgctcctgg acctattttg aggggtgagg tctttgatgg tatagaggca    1440
gtccgtaagt tggagagttg gttgattgaa aaccatggat tccagccaca atacgctgtc    1500
tctgagctga cggagaagaa cttctggagg atgtttgatg gaagcctata cgagaactgc    1560
agaaaaaagt acagagccat cggaaccttc atgagtgtgt actataagtc taagaaagga    1620
aagaagaccg agaaggaggt gcaggacgct gagcaagaga ctgctgaagt tgagacccca    1680
gaagttgatg agcctgaaga ttga                                          1704
```

<210> SEQ ID NO 7
<211> LENGTH: 1857
<212> TYPE: DNA
<213> ORGANISM: Solanum tuberosum

<400> SEQUENCE: 7

```
atgtcggatg ctaaggcccc cgcggccgcc gttcacccta ggaggaagat ccagttggtg      60
gactttcttc tttcgttccg atggatcatt gttatctttt ttgtccttcc attctcgttc     120
ttgtattact tctccatata tctaggggat ttgaagtctg agaagaaatc ttacaagcaa     180
cgccagatgg aacacgatga aatgttaaa gaggttgtga agcgccttga acagaggaat      240
gcagaaaagg atggtcttgt ctgcacggcc aggcctcctt gggttgttgt tggaatgaga     300
aacgtagact ataaacgtgc tcgtcatttt gaagttgatc tttctaagtt tagaaatata     360
cttgatattg acacggaacg tatggttgcc aaagttgagc ctcttgtcaa tatgggccaa     420
atgtcaaggg tcgccatccc aatgaatctt ccccttgcag ttcttgctga gcttgatgat     480
cttaccgttg gaggtttgat caatgggttc ggggtcgaag aagttctca catctttgga     540 ttgttctctg acactgttgt agcacttgag gttgttctag ctgatggaaa ggttgttaga     600
gctacaaagg acaacgaata ttctgatctt ttctacgcta ttccgtggtc tcaagggaca     660
ttggggcttc ttgtttcagc tgaaatcaag cttataccag ttgatcaata cgtaaaactt     720
acctacaaac ctgtaagggg taatcttcaa gagcttgcac aggcttacgc ggattctttt     780
gcacctaaag atggagatca ggacaatcct tctaaagttc cagagatggt agaaggcatg     840
atttatggtc caacagaagg tgttatgatg accggtatgt atgcttcgag gaatgaagcc     900
aaacgaaggg gtaatgtaat caacaattat ggttggtggt caaaccatg gttttaccaa      960 cacgctcaaa ccgcactgaa aagagggaa tttgtggagt acatcccaac tagggactac    1020
taccacaggc acacgagatc gttgtattgg gaagggaaac taattcttcc atttggtgat    1080
cagttctggt ttaggttcct cttaggatgg ctcatgccac caaagattgc tctgctcaaa    1140
```

-continued

```
gccacacaaa gtgaggctat tagaaactat taccatgacc atcatgtcat tcaggatctg    1200
cttgttcctc tttacaaggt cggcgattgt ctcgagtggg ttcaccgcga gatggaggta    1260
aaactcttag tccttttttt agtccgtttt ttggttttg gcaactctta acggaagaaa    1320
gtatttgatt tatgttcaag atatacaaag attatgcatc acataatctg attgtatttg    1380
aattgaattg aatttgttta ggtatatccc atttggctct gcccacacag aatttacaag    1440
ctgcctgtga gacctatgat ctaccctgaa ccaggattcg agaaacacaa aaggcagggt    1500
gacaccgaat atgcacaaat gtacactgat attggtgtct actatgttcc cggagcagtc    1560
ctgaggggtg agccatttga tggatcagag aaatgccgcc aacttgagct ttggttgatt    1620
gaaaaccatg gatttcaggc tcaatacgcg gtgactgagc tgacagagaa gaatttctgg    1680
aggatgtttg ataacagtct gtacgagcaa tgcagaagga agtacaaagc tattggaacg    1740
ttcatgagtg tgtactataa atcgaagaaa ggaaggaaga cagagaagga agtgcaggaa    1800
gctgagcaag agaaagctga acaagagact cctgaagctg atgaacctgc gaattga      1857
```

<210> SEQ ID NO 8
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 8
caccatgtcg gatgctaagg ccc                                             23

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 9
tcaattcgca ggttcatcag                                                 20

<210> SEQ ID NO 10
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 10
caccatgaca gatgttcagg ctcc                                            24

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 11
tcaatcttca ggctcatcaa ct                                              22

<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide primer

```
<400> SEQUENCE: 12
gagctctaga ccctaggagg aagatccag                                          29

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 13
ggatccatat gcgtttctca ttccaacaac a                                       31

<210> SEQ ID NO 14
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 14
taaagcacga ggaagcggt                                                     19

<210> SEQ ID NO 15
<211> LENGTH: 19
<212> TYPE: DNA
<213> ORGANISM: Artificial Sequence
<220> FEATURE:
<223> OTHER INFORMATION: Synthetic oligonucleotide primer

<400> SEQUENCE: 15
gcacaacaga caatcggct                                                     19

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 16
ctctgctcaa agccacacaa                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 17
tcaattcgca ggttcatcag                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 18
ctctgctcaa agccacacaa                                                    20

<210> SEQ ID NO 19
```

```
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 19
ccgttaagag ttgccaaaaa cc                                          22

<210> SEQ ID NO 20
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 20
caaattttga atggaggggt at                                          22

<210> SEQ ID NO 21
<211> LENGTH: 570
<212> TYPE: PRT
<213> ORGANISM: Solanum tuberosum

<400> SEQUENCE: 21
```

Met Ser Asp Ala Lys Ala Pro Ala Ala Thr Val His Pro Arg Arg Lys
1               5                   10                  15

Ile Gln Leu Val Asp Phe Leu Leu Ser Phe Arg Trp Ile Ile Val Ile
            20                  25                  30

Phe Phe Val Leu Pro Phe Ser Phe Leu Tyr Tyr Phe Ser Ile Tyr Leu
        35                  40                  45

Gly Asp Leu Lys Ser Glu Lys Lys Ser Tyr Lys Gln Arg Gln Met Glu
    50                  55                  60

His Asp Glu Asn Val Lys Glu Val Val Lys Arg Leu Gly Gln Arg Asn
65                  70                  75                  80

Ala Glu Lys Asp Gly Leu Val Cys Thr Ala Arg Pro Pro Trp Val Val
                85                  90                  95

Val Gly Met Arg Asn Val Asp Tyr Lys Arg Ala Arg His Phe Glu Val
            100                 105                 110

Asp Leu Ser Lys Phe Arg Asn Ile Leu Asp Ile Asp Thr Glu Arg Met
        115                 120                 125

Val Ala Lys Val Glu Pro Leu Val Asn Met Gly Gln Met Ser Arg Val
    130                 135                 140

Thr Ile Pro Met Asn Leu Ser Leu Ala Val Leu Ala Glu Leu Asp Asp
145                 150                 155                 160

Leu Thr Val Gly Gly Leu Ile Asn Gly Phe Gly Val Glu Gly Ser Ser
                165                 170                 175

His Ile Phe Gly Leu Phe Ser Asp Thr Val Val Ala Leu Glu Val Val
            180                 185                 190

Leu Ala Asp Gly Lys Val Val Arg Ala Thr Lys Asp Asn Glu Tyr Ser
        195                 200                 205

Asp Leu Phe Tyr Ala Ile Pro Trp Ser Gln Gly Thr Leu Gly Leu Leu
    210                 215                 220

Val Ser Ala Glu Ile Lys Leu Ile Pro Val Asp Gln Tyr Val Lys Leu
225                 230                 235                 240

Thr Tyr Lys Pro Val Arg Gly Asn Leu Lys Glu Leu Ala Gln Ala Tyr
                245                 250                 255

Ala Asp Ser Phe Ala Pro Lys Asp Gly Asp Gln Asp Asn Pro Ser Lys

```
                    260                 265                 270
Val Pro Glu Met Val Glu Gly Met Ile Tyr Gly Pro Thr Glu Gly Val
            275                 280                 285
Met Met Thr Gly Met Tyr Ala Ser Lys Lys Glu Ala Lys Arg Arg Gly
        290                 295                 300
Asn Val Ile Asn Asn Tyr Gly Trp Trp Phe Lys Pro Trp Phe Tyr Gln
305                 310                 315                 320
His Ala Gln Thr Ala Leu Lys Arg Gly Glu Phe Val Glu Tyr Ile Pro
                325                 330                 335
Thr Arg Asp Tyr Tyr His Arg His Thr Arg Ser Leu Tyr Trp Glu Gly
            340                 345                 350
Lys Leu Ile Leu Pro Phe Gly Asp Gln Phe Trp Phe Arg Phe Leu Leu
        355                 360                 365
Gly Trp Leu Met Pro Pro Lys Ile Ala Leu Leu Lys Ala Thr Gln Ser
    370                 375                 380
Glu Ala Ile Arg Asn Tyr Tyr His Asp His His Val Ile Gln Asp Leu
385                 390                 395                 400
Leu Val Pro Leu Tyr Lys Val Gly Asp Cys Leu Glu Trp Val His Arg
                405                 410                 415
Glu Met Glu Val Tyr Pro Ile Trp Leu Cys Pro His Arg Ile Tyr Lys
            420                 425                 430
Leu Pro Val Arg Pro Met Ile Tyr Pro Glu Pro Gly Phe Glu Lys His
        435                 440                 445
Lys Arg Gln Gly Asp Thr Glu Tyr Ala Gln Met Tyr Thr Asp Val Gly
    450                 455                 460
Val Tyr Tyr Val Pro Gly Ala Val Leu Arg Gly Glu Pro Phe Asp Gly
465                 470                 475                 480
Ser Glu Lys Cys Arg Gln Leu Glu Leu Trp Leu Ile Glu Asn His Gly
                485                 490                 495
Phe Gln Ala Gln Tyr Ala Val Thr Glu Leu Thr Glu Lys Asn Phe Trp
            500                 505                 510
Arg Met Phe Asp Asn Ser Leu Tyr Glu Gln Cys Arg Arg Lys Tyr Lys
        515                 520                 525
Ala Ile Gly Thr Phe Met Ser Val Tyr Tyr Lys Ser Lys Lys Gly Arg
    530                 535                 540
Lys Thr Glu Lys Glu Val Gln Glu Ala Glu Gln Glu Lys Ala Glu Gln
545                 550                 555                 560
Glu Thr Pro Glu Ala Asp Glu Pro Ala Asn
                565                 570

<210> SEQ ID NO 22
<211> LENGTH: 1710
<212> TYPE: DNA
<213> ORGANISM: Solanum tuberosum

<400> SEQUENCE: 22
atgtcggatg ctaaggcccc cgcggccacc gttcacccta ggaggaagat ccagttggtg      60
gactttcttc tttcgttccg atggatcatt gttatctttt tgttcttcc attctcgttc     120 ttgtattact tctccatata tctaggggat ttgaagtctg agaagaaatc ttacaagcaa     180
cgccagatgg aacacgatga gaatgttaaa gaggttgtga agcgccttgg acagaggaat     240
gcagaaaagg atggtcttgt ctgcacggcc aggcctcctt gggttgttgt tggaatgaga     300
aacgtagact ataaacgtgc tcgtcatttt gaagttgatc tttctaagtt tagaaatata     360
```

```
cttgatattg acacagaacg tatggttgct aaagttgagc ctcttgtcaa tatgggccaa        420
atgtcaaggg tcaccatccc aatgaatctt tcccttgcag ttcttgctga gcttgatgat        480
cttaccgttg gtggtttgat caatgggttc ggggtcgaag gaagttctca catctttgga        540
ttgttctctg acactgttgt agcacttgag gttgttctag ctgatggaaa ggttgttaga        600
gctacaaagg acaacgaata ttctgatctt ttctacgcta ttccgtggtc tcaagggaca        660
ttggggcttc ttgtttcagc tgaaatcaag cttataccag ttgatcaata cgtaaaactt        720
acctacaaac ctgtaagggg taatcttaaa gagcttgcac aggcttatgc ggattctttt        780
gcacctaaag atggagatca ggacaatcct tctaaagttc cagagatggt agaaggcatg        840
atttatggtc caacggaagg tgttatgatg accggtatgt atgcttcgaa gaaagaagcc        900
aaacgaaggg gtaatgtaat caacaattat ggttggtggt tcaaaccatg gttttaccaa        960
cacgctcaaa ctgcactgaa aagagggaa tttgtggagt acatcccaac tagggactac       1020
taccacaggc acacgagatc gttgtattgg gaagggaaac taattcttcc atttggtgat       1080
cagttctggt ttaggttcct cttaggatgg ctcatgccac caaagattgc tttgctcaaa       1140
gccacccaaa gtgaggctat tagaaactat taccatgacc atcatgtcat tcaggatctg       1200
cttgttcctc tttacaaggt cggcgattgt ctcgagtggg ttcaccgcga gatggaggta       1260 tatcccatt ggctctgccc acacagaatt tacaagctgc ctgtgagacc tatgatctac        1320
cctgaaccag gattcgagaa acacaaaagg cagggtgaca ccgaatatgc acaaatgtac       1380
actgatgttg gtgtgtacta tgttccggga gcagtgctga ggggtgagcc atttgatggt       1440
tcagagaaat gccgccaact tgagctttgg ttgatagaaa accatggatt tcaggctcaa       1500
tacgcggtga ctgagctgac agagaagaat ttctggagga tgtttgataa cagtttgtac       1560
gagcaatgca gaaggaagta caaagctatc ggaacgttca tgagtgtgta ctataaatcg       1620
aagaaaggaa ggaagacaga gaaggaagtg caggaagctg agcaagagaa agctgaacaa       1680
gagactcctg aagctgatga acctgcgaat                                        1710
```

US 9,688,995 B2

GENE ENCODING ENZYME THAT REDUCES POSITION 24 OF STEROID SKELETON AND PLANT IN WHICH EXPRESSION LEVEL OF THE GENE IS LOWERED

CROSS REFERENCE TO RELATED APPLICATIONS

This application is a National Stage of International Application No. PCT/JP2013/058418 filed Mar. 22, 2013, claiming priority based on Japanese Patent Application No. 2012-068039 filed Mar. 23, 2012, the contents of all of which are incorporated herein by reference in their entirety.

TECHNICAL FIELD

The present invention relates to an enzyme that reduces position 24 of the steroid skeleton of a plant belonging to the family Solanaceae, such as a potato, DNA encoding the enzyme that reduces position 24 of the steroid skeleton, a method for breeding and selecting a novel plant belonging to the family Solanaceae, such as a potato, using such DNA, and a plant belonging to the family Solanaceae, such as a potato, which does not accumulate glycoalkaloids because of the suppressed expression of the gene encoding the enzyme or the altered activity of the enzyme.

BACKGROUND ART

Glycoalkaloids are a group of plant-derived compounds, which are also referred to as steroidal alkaloids. The glycoalkaloid structure is composed of C27 isoprenoids containing a nitrogen atom, and it has been reported that there are 422 compounds of glycoalkaloids from plants belonging to the genus *Solanum* (Non-Patent Literature 1, chapter 7.8). As to a plant other than those belonging to the genus *Solanum* in the family Solanaceae, some plants belonging to the family Liliaceae are also known to contain glycoalkaloids. Among glycoalkaloids, important ones are chaconine and solanine from potatoes (*Solanum tuberosum*), and tomatine from tomatoes (*Solanum lycopersicum*), which belong to the genus *Solanum* in the family Solanaceae.

Potato is the fourth most produced crop in the world following corn, rice, and wheat. However, it is a well-known fact that toxic chaconine and solanine are contained in the buds coming out of the tubers or the aerial parts of the plants. Symptoms of poisoning such as abdominal pain, dizziness, and mild disturbance of consciousness are caused by chaconine or solanine. Chaconine and solanine are easily accumulated in tubers when the tubers are damaged or exposed to solar light, and thus there is a risk of poisoning accident caused by improper management of tubers.

These poisoning accidents frequently happen, and recently, a glycoalkaloid poisoning accident occurred at an elementary school in Nara City, Japan on Jul. 16, 2009 (reported by Asahi.com). Potatoes are usually safe foods because they are managed such that the content of glycoalkaloid is maintained at 20 mg/100 g or less by storing potato tubers in a dark place etc. However, in consideration of the risk of such a poisoning accident described above, reducing glycoalkaloids in potato is a matter of concern to all of the persons who deal with potatoes such as the breeding, production, storage, transportation, sale, and purchase of potatoes, but has not been achieved to date. The reasons are as follows. A wild potato species with no glycoalkaloids has not been found, the biosynthetic pathway of glycoalkaloids has remained unconfirmed (FIGS. 7.24A and 7.24B of Non-patent Literature 1, and Non-patent Literature 2), and the identification of genes involved in the biosynthetic pathway has not been proceeded.

Glycoalkaloids exhibit toxicity such as cholinesterase inhibitory activity or membrane disruption effect, but in addition to this, it is known that glycoalkaloids exhibit medicinal effects such as anti-cancer activity, a liver protective effect, an antispasmodic effect, an immune system promoting effect, an antifungal effect, an antiprotozoal effect, and shellfish killing agent activity (Non-patent Literature 1). It has also been reported that esculeoside A, which is a metabolite of glycoalkaloids in tomato, exhibits various physiological effects (Non-patent Literature 3). However, research and development on suppressing the metabolites or efficient production thereof have hardly proceeded since the biosynthetic pathway thereof is not known.

Several enzyme genes catalyzing the transglycosylation process following the aglycone biosynthesis process have been reported (Non-patent Literature 4 to Non-patent Literature 6). However, in Non-patent Literature 4, the gene of UDP-galactosyltransferase, which mediates the conversion of solanidine, which is aglycone, to γ solanine, and a strain in which the gene is suppressed have been reported, but the production of chaconine has not been suppressed at all (FIG. 2 of Non-patent Literature 4). In Non-patent Literature 4, the gene of UDP-glucosyltransferase, which mediates the conversion of solanidine to γ chaconine, and a strain in which the gene is suppressed have been reported, but the production of both chaconine and solanine is hardly suppressed (FIG. 5 of Non-patent Literature 5). In Non-patent Literature 6, the gene of rhamnosyl transferase, which mediates the conversion of β chaconine to α chaconine and β solanine to α solanine, has been reported, but the β-form and γ-form are increased by the suppression of the gene, although the α-form is decreased. As seen from these, by the suppression of the transglycosylation process, the molecular species of glycoalkaloids can be changed but it is very difficult to control the total amount of glycoalkaloids. Recently, an enzyme gene, which catalyzes the oxidative pathway involved in the biosynthetic pathway of glycoalkaloids, has been reported (Patent Literature 1). However, the specific enzyme reaction has remained unclear.

There is a report of an attempt to decrease glycoalkaloids by overexpressing biosynthetic genes of plant sterols or plant hormones (Non-patent Literature 7). However, the amount of glycoalkaloids can only be reduced to about a half at most, and thus an effective means has not been provided in modifying the pathway (FIG. 5 of Non-patent Literature 7).

Plants mainly produce plant sterols after the introduction of a methyl group into position 24. As a biosynthetic gene for such process, a DWF1 gene of *Arabidopsis thaliana* has been known (Non-Patent Literatures 8 and 9), and the enzymatic reaction reduces Δ24 (28) of the steroid (i.e., a double bond between C24 and C28); that is, such enzyme catalyzes a reaction for reducing methylene or the like at position 24. It is known that the DWF1 gene has a low homology with a DHCR24 gene of an enzyme that reduces a double bond at position 24 (Δ24; a double bond between C24 and C25) of the human steroid skeleton (i.e., the 3β-hydroxycholesterol Δ24-reducing enzyme). In contrast, in addition to plant sterols, production of cholesterol is observed in a plant belonging to the family Solanaceae (Non-Patent Literature 10). However, the biosynthetic pathway thereof remains unknown, and it has been predicted that a cholesterol would be a starting material of a glycoalkaloid biosynthetic pathway (Non-Patent Literatures 11 and 12), although such prediction has not yet been validated.

PRIOR ART LITERATURE

Patent Literatures

Patent Literature 1: WO 2011/025011

Non-Patent Literatures

Non-Patent Literature 1: Eich, Solanaceae and Convolvulaceae: Secondary Metabolite, 2008, Springer
Non-Patent Literature 2: Ginzberg et al., Potato Research, 2009, 52: 1-15
Non-Patent Literature 3: Nohara et al., J. Nat. Prod., 2010, 73: 1734-1741
Non-Patent Literature 4: McCue et al., Plant Sci., 2005, 168: 267-273
Non-Patent Literature 5: McCue et al., Phytochemistry, 2006, 67: 1590-1597
Non-Patent Literature 6: McCue et al., Phytochemistry, 2007, 68: 327-334
Non-Patent Literature 7: Arnqvist et al., Plant Physiol., 2003, 131: 1792-1799
Non-Patent Literature 8: Choe et al., Plant Physiol., 1999, 119: 897-907
Non-Patent Literature 9: Klahre et al., Plant Cell, 1998, 10: 1677-1690
Non-Patent Literature 10: Heftmann, Phytochemistry, 1983, 22: 1843-1860
Non-Patent Literature 11: Eckart Eich, "Solanaceae and Convolvulaceae: Secondary Metabolite," 2008, Springer, Heidelberg, Germany, pp. 368-373
Non-Patent Literature 12: Kaneko et al., Phytochemistry, 1977, 16: 791-793

SUMMARY OF THE INVENTION

Objects to be Attained by the Invention

The present invention provides an enzyme that reduces position 24 of the steroid skeleton, DNA encoding the enzyme that reduces position 24 of the steroid skeleton, a method for breeding and selecting a novel plant belonging to the family Solanaceae using the DNA, and a plant belonging to the family Solanaceae, which does not produce cholesterols, including glycoalkaloids, because of the suppressed expression of the gene encoding the enzyme or the altered activity of the enzyme.

Means for Attaining the Objects

The present inventors have conducted concentrated studies in order to attain the above objects. The present inventors focused on the assumption such that cholesterol would serve as a starting material for glycoalkaloid biosynthesis. The sterol methyltransferase 1 gene had been deduced to differentiate a plant sterol from cholesterol and studied (Non-Patent Literature 7). The present inventors, however, focused on the cholesterol synthetase that reduces a double bond at position 24 (i.e., Δ24: a double bond between C24 and C25) of the steroid skeleton (i.e., 3β-hydroxycholesterol Δ24-reducing enzyme; a position-24-reducing enzyme) and discovered a candidate gene in silico, and they suppressed the expression of the endogenous candidate gene by causing expression of parts of the candidate genes to induce RNAi.

As a result, they successfully obtained a potato transformant with significantly reduced glycoalkaloid content and, at the same time, identified the glycoalkaloid biosynthetic enzyme gene. Also, they demonstrated acquisition of a glycoalkaloid-free plant belonging to the family Solanaceae such as a potato by selecting a plant in which the expression of the above gene is suppressed. They also demonstrated that comparison of the genome sequence of the above-mentioned gene among various plants belonging to the family Solanaceae would enable the polymorphism analysis and production of a novel plant belonging to the family Solanaceae. This has led to the completion of the present invention. They also succeeded in producing tomatoes with reduced glycoalkaloid content through suppression of the endogenous gene in tomatoes in a similar manner.

Specifically, the present invention includes the following.
[1] A method for producing a plant with a reduced risk for accumulation of glycoalkaloids, comprising suppressing the activity of an enzyme that reduces position 24 of the steroid skeleton of a plant belonging to the family Solanaceae or suppressing the expression of a gene encoding the enzyme.
[2] The method according to [1], wherein the plant is a cultivated plant.
[3] The method according to [1] or [2], wherein the enzyme is either protein (a) or (b) below:
(a) a protein consisting of the amino acid sequence as shown in SEQ ID NO: 1 or 21; or
(b) a protein consisting of an amino acid sequence derived from the amino acid sequence as shown in SEQ ID NO: 1 or 21 by deletion, substitution, insertion, or addition of one or several amino acids and reducing position 24 of the steroid skeleton of a plant belonging to the family Solanaceae.
[4] The method according to [1] or [2], wherein the enzyme is encoded by a gene consisting of any of DNAs (c) to (f) below:
(c) DNA consisting of the nucleotide sequence as shown in SEQ ID NO: 2 or 22;
(d) DNA hybridizing under stringent conditions to DNA consisting of a nucleotide sequence complementary to DNA consisting of the nucleotide sequence as shown in SEQ ID NO: 2 or 22 and encoding a protein having activity of reducing position 24 of the steroid skeleton of a plant belonging to the family Solanaceae;
(e) DNA consisting of a nucleotide sequence having 80% or higher sequence identity with the nucleotide sequence as shown in SEQ ID NO: 2 or 22 and encoding a protein that reduces position 24 of the steroid skeleton of a plant belonging to the family Solanaceae; and
(f) DNA consisting of a degenerate isomer comprising the nucleotide sequence as shown in SEQ ID NO: 2 or 22.
[5] The method according to [1] or [2], wherein the enzyme is protein (g) or (h) below:
(g) a protein consisting of the amino acid sequence as shown in SEQ ID NO: 3; or
(h) a protein consisting of an amino acid sequence derived from the amino acid sequence as shown in SEQ ID NO: 3 by deletion, substitution, insertion, or addition of one or several amino acids and reducing position 24 of the steroid skeleton of a plant belonging to the family Solanaceae.
[6] The method according to [1] or [2], wherein the enzyme is encoded by a gene comprising any of DNAs (i) to (l) below:
(i) DNA consisting of the nucleotide sequence as shown in SEQ ID NO: 4;

(j) DNA hybridizing under stringent conditions to DNA consisting of a nucleotide sequence complementary to DNA consisting of the nucleotide sequence as shown in SEQ ID NO: 4 and encoding a protein that reduces position 24 of the steroid skeleton of a plant belonging to the family Solanaceae;

(k) DNA consisting of a nucleotide sequence having 80% or higher homology to the nucleotide sequence as shown in SEQ ID NO: 4 and encoding a protein that reduces position 24 of the steroid skeleton of a plant belonging to the family Solanaceae; and (l) DNA consisting of a degenerate isomer of the nucleotide sequence as shown in SEQ ID NO: 4.

[7] The method according to [1] or [2], wherein the enzyme activity or the gene expression is suppressed by genetic recombination.

[8] The method according to [1] or [2], wherein the enzyme activity or the gene expression is suppressed by deletion of a gene that encodes the enzyme.

[9] The method according to [1] or [2], which comprises selecting a progeny obtained by crossing involving the use of a plant in which the enzyme activity or the gene expression is suppressed as a mother plant.

[10] The method according to [9], wherein the mother plant is obtained by artificial modification of the enzyme gene via mutation.

[11] The method according to [9], wherein the mother plant is obtained by screening of wild-type plants.

[12] The method according to [9], wherein the mother plant is obtained and the progeny is selected by detecting the presence of a mutation or polymorphism in the enzyme gene.

[13] The method according to [12], wherein the detection of the presence of a mutation or polymorphism comprises steps of:

(i) isolating a nucleic, acid, which is genomic DNA or RNA, from a plant;

(ii) synthesizing cDNA by reverse transcription when the nucleic acid of (i) is RNA;

(iii) amplifying a gene fragment comprising at least a part of the nucleotide sequence as shown in SEQ ID NO: 2, 4, 7, or 22 from DNA obtained in the step (i) or (ii); and (iv) determining the presence of a mutation or polymorphism in DNA.

[14] A cultivated plant produced by the method according to any of [1] to [13].

[15] The cultivated plant according to [14], which is a potato.

[16] A gene marker sequence used in the method according to [13].

[17] A primer sequence for gene amplification used in the method according to [13].

[18] A cultivated plant comprising a mutation in a gene encoding an enzyme that reduces position 24 of the steroid skeleton of a plant belonging to the family Solanaceae and having a reduced risk of accumulation of glycoalkaloids.

[19] The cultivated plant according to [18], which does not accumulate glycoalkaloids.

The present specification encompasses the contents of the specification and/or drawings of JP patent Application No. 2012-068039, based on which the present application claims priority.

Advantageous Effects of Invention

According to the present invention, the expression of the activity of a protein having activity of reducing position 24 of the steroid skeleton of a plant belonging to the family Solanaceae and that of the gene encoding such protein can be regulated. Specifically, the present invention provides a method for producing a plant in which the activity of such gene is regulated and a plant belonging to the family Solanaceae that does not accumulate cholesterols, including glycoalkaloids.

BRIEF DESCRIPTION OF DRAWINGS

FIG. 1 shows the results of analysis of amino acid sequence homology between StDWF1H (SEQ ID NO: 1) and StDWF1 (SEQ ID NO:2) using GENETYX (Genetyx Corporation). Sequence identity of 80.0% is observed for 562 amino acids.

EMBODIMENTS FOR CARRYING OUT THE INVENTION

Figure 2:
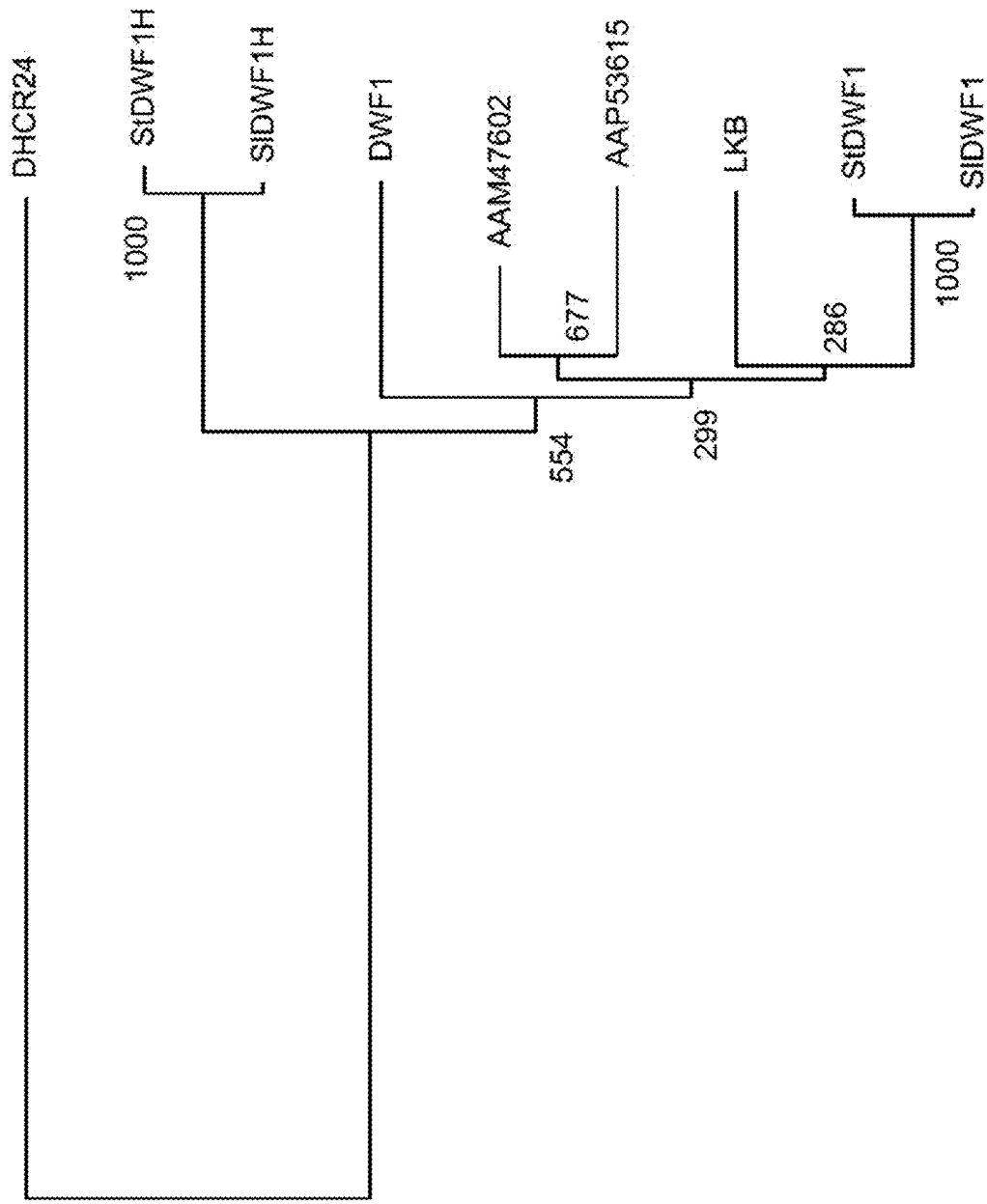
FIG. 2 shows the results of molecular phylogenetic analysis of genes comprising amino acid sequences homologous to those of DWF1. Numerical values are relative to the results of the Bootstrap test 1,000.

Hereafter, the present invention is described in detail.

1. Enzymatic Protein that Reduces Position 24 of Steroid Skeleton (Position-24-Reducing Enzyme)

The glycoalkaloid biosynthetic enzyme according to the present invention is a protein having enzymatic activity for reducing a double bond at position 24 (Δ24, a double bond between C24 and C25) of the steroid skeleton, and such enzyme is essential for cholesterol synthesis. Accordingly, the enzyme according to the present invention can also be expressed as a cholesterol synthetic enzyme, 3β-hydroxycholesterol Δ24-reducing enzyme, or position-24-reducing enzyme. The enzyme according to the present invention is capable of reducing position 24 of a compound having a double bond at position 24 of the steroid skeleton of a cholestane derivative, such as desmosterol (cholesta-5,24-dienol), 7-dehydrodesmosterol (cholesta-5,7,24-trienol), lanosterol (lanosta-8,24-dienol), or cycloartenol (cycloarta-24-enol). In the present description, such enzymatic activity is referred to as "activity of position-24-reducing enzyme," and an enzyme having such enzymatic activity is referred to as a "position-24-reducing enzyme." The enzymatic protein according to the present invention is a reducing enzyme having a transmembrane region and an FAD-binding sequence.

Examples of plants containing such enzymes include plants that generate cholesterols, such as plants of the family Solanaceae, such as potatoes (*Solanum tuberosum*), tomatoes (*Solanum lycopersicum*), and *Solanum glaucophyllum*, those of the family Scrophulariaceae, such as digitalis (*Digitalis purpurea*), those of the family Dioscoreacea, such as yam (*Dioscorea* sp.), and those of the family Labiatae, such as Ajuga reptans.

A compound in which position 24 has been reduced by the enzyme according to the present invention comprises cholesterols synthesized by plants or substituted derivatives thereof. Examples thereof include cholesterol (cholesta-5-enol), 7-dehydrocholesterol (cholesta-5,7-dienol), a salt of either thereof, and a substituted derivative of either thereof.

Examples of salts include alkali metal salts, such as sodium salt and potassium salt, ammonium salts, such as salts of ammonia or an organic amine, such as aliphatic amine, aromatic amine, saturated amine, or unsaturated amine, and carboxylic acid salt. Such salts may be formed during the process of production of the target triterpene compound by the method of the present invention. Alternatively, salts may be formed via neutralization after the production of such compound.

Examples of substituted derivatives include compounds derived from steroid compounds via substitution of a hydrogen atom at a position that is considered to be less influential on the activity of position-24-reducing enzyme, such as position 1, 2, 4, 6, 7, 11, 12, 14, 16, 17, 18, 19, 21, 22, 23, 26, or 27, with another substituent, such as a functional group, such as a lower alkyl group (e.g., methyl, ethyl, propyl, or butyl), halogen (e.g., fluorine, chlorine, bromine, or iodine), a hydroxyl group, an ester group (e.g., acetoxy or propanoyloxy), an acyl group (e.g., formyl, acetyl, or propionyl), an alkoxy group (e.g., methoxy, ethoxy, or propoxy), an amino group, a mono- or di-lower alkylamino group (e.g., methylamino, dimethylamino, or ethylamino), an amide group, a lower alkylamide group (e.g., acetamide), an oxo group, a cyano group, a nitro group, a lower alkylthio group (e.g., methylthio or ethylthio), and a sulfonyl group (e.g., mesyl or ethyl sulfonyl). In the present invention, cholesterol and a cholesterol derivative are collectively referred to as "cholesterols."

Figure 5:
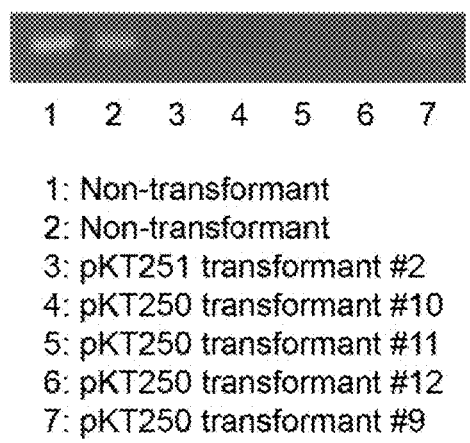
FIG. 5 shows the results of RT-PCR of RNA extracted from the in vitro stems of potato transformants.

Examples of preferable steroid compounds that serve as substrates for the position-24-reducing enzyme according to the present invention include steroid compounds, such as desmosterol, 7-dehydrodesmosterol, and substituted derivatives of either thereof. The site of substitution and the substituents for the substituted derivative are as described above. By the method of the present invention, a steroid compound can be obtained from a substrate compound in which a double bond at position 24 has been reduced with the aid of the position-24-reducing enzyme. As an example, a reaction that reduces a double bond at position 24 of desmosterol is shown in FIG. 5. Cholesterol is generated by reducing a double bond at position 24 of the steroid skeleton of desmosterol, and 7-dehydrocholesterol is generated by reducing a double bond at position 24 of the steroid skeleton of 7-dehydrodesmosterol. Further, vitamin D3 is generated upon irradiation of 7-dehydrocholesterol with light such as ultraviolet rays. In the present invention, vitamin D3 and vitamin D3 derivatives are collectively referred to as "vitamin D3s." A vitamin D3 derivative has a substituent similar to that for the derivative of the steroid compound.

A substrate for a position-24-reducing enzyme having a double bond is synthesized as follows. That is, lanosterol or cycloartenol is synthesized from 2,3-oxidosqualene with the aid of a lanosterol synthetic enzyme or cycloartenol synthetic enzyme, and a fundamental steroid skeleton is then synthesized. Thus, a substrate of interest is synthesized (P. M. Dewick, Medicinal Natural Product, 3rd ed., John Wiley & Sons, 2009). Sequences of such synthetic enzymes have already been identified via cloning from cDNA libraries of various types of animals, plants and bacteria, and such sequences have already been known. Lanosterol synthetic enzymes are described in, for example, Baker et al., 1995, Biochem. Biophys. Res. Commun., 213: 154-160; Sung et al., 1995, Bio. Pharm. Bull., 18: 1459-1461; Corey et al., 1994, Proc. Natl. Acad. Sci., U.S.A., 91: 2211-2215; and Shi et al., 1994, Proc. NatI. Acad. Sci., U.S.A., 91: 7370-7374. Cycloartenol synthetic enzymes are described in, for example, Corey et al., 1993, Proc. Natl. Acad. Sci., U.S.A., 90: 11628-11632. Such synthetic enzymes are known to exist in animals, plants, and bacteria, such as humans, mice, rats, yeasts, koji mold, *Arabidopsis thaliana*, *Oryza sativa*, *Populus nigra*, *Vitis vinifera*, *Hordeum vulgare*, *Solanum lycopersicum*, and *Glycine max*. Thus, DNA encoding the lanosterol synthetic enzyme or cycloartenol synthetic enzyme may be obtained from such organisms in accordance with the cloning technique described in the aforementioned literature, and such DNA may be introduced into microbial, bacterial, or plant cells via well-known DNA recombination techniques or PCR techniques, so as to express such synthetic enzymes, according to need. In addition, DNA encoding a position-24-reducing enzyme may be expressibly incorporated into transgenic bacteria or plants regenerated from the transformed bacterial cells or plant cells capable of expressing lanosterol synthetic enzymes or cycloartenol synthetic enzymes. Thus, steroid compounds in which position 24 has been reduced, such as cholesterol or 7-dehydrocholesterol, can be generated with the use of the cells, bacteria, and plants described above.

Examples of position-24-reducing enzymes that can be used in the present invention include, but are not limited to, enzymes comprising the amino acid sequences as shown in SEQ ID NO: 1, SEQ ID NO: 21, and SEQ ID NO: 3, respectively, derived from potatoes and tomatoes. Further, a protein comprising an amino acid sequence having some mutations in the amino acid sequence as shown in SEQ ID NO: 1, SEQ ID NO: 21, or SEQ ID NO: 3 and having activity of position-24-reducing enzyme is within the scope of the enzyme that can be used in the present invention. A potato-derived position-24-reducing enzyme is referred to as "StDWF1H," and a tomato-derived position-24-reducing enzyme is referred to as "SlDWF1H."

Examples of "an amino acid sequence having some mutations" include an amino acid sequence derived from the amino acid sequence as shown in SEQ ID NO: 1, SEQ ID NO: 21, or SEQ ID NO: 3 by deletion, substitution, insertion, and/or addition of one or more, and preferably one or several, such as 1 to 10, preferably 1 to 7, more preferably 1 to 5, further preferably 1 to 3, and still further preferably 1 or 2 amino acids and an amino acid sequence having at least 60%, at least 70%, at least 80%, at least 85%, preferably at least 90%, more preferably at least 95%, and particularly preferably at least 97%, 98%, or 99% sequence identity with the above amino acid sequence, when calculated with the use of known algorithms for homology search, such as BLAST or FASTA (based on, for example, default, (namely, initially set) parameters). Sequence identity among the enzymatic proteins comprising the amino acid sequences as shown in SEQ ID NO: 1, SEQ ID NO: 21, and SEQ ID NO: 3 is about 70% to 80%.

In this description, "sequence identity" is expressed in percentage (%) terms, representing the number of identical amino acids or nucleotides relative to the total number of amino acids or nucleotides containing gaps determined when, for example, two amino acid sequences or nucleotide sequences are aligned. (Gaps may or may not be introduced, and gaps are preferably introduced.)

The position-24-reducing enzyme according to the present invention encompasses a naturally occurring position-24-reducing enzyme isolated from a plant and a recombinant position-24-reducing enzyme produced via genetic engineering.

2. DNA Encoding Position-24-Reducing Enzyme

The term "DNA" used herein refers to any of genomic DNA, a gene, cDNA, and a chemically modified DNA.

DNA encoding a position-24-reducing enzyme that is used in the present invention is DNA encoding an enzyme having activity of reducing position 24 of the steroid skeleton.

Examples of DNAs encoding a position-24-reducing enzyme include DNA comprising the nucleotide sequence encoding the amino acid sequence as shown in SEQ ID NO: 1, DNA comprising the nucleotide sequence encoding the amino acid sequence as shown in SEQ ID NO: 21, and DNA comprising the nucleotide sequence encoding the amino acid sequence as shown in SEQ ID NO: 3. Specific examples thereof include DNA comprising the nucleotide sequence as shown in SEQ ID NO: 2, DNA comprising the nucleotide sequence as shown in SEQ ID NO: 4, and DNA comprising the nucleotide sequence as shown in SEQ ID NO: 22.

Examples of DNA encoding a position-24-reducing enzyme that can be used in the present invention include DNA hybridizing under stringent conditions to DNA comprising a nucleotide sequence complementary to the nucleotide sequence as shown in SEQ ID NO: 2, SEQ ID NO: 4, or SEQ ID NO: 22, DNA having at least 60%, at least 70%, at least 80%, at least 85%, preferably at least 90%, more preferably at least 95%, and particularly preferably at least 97%, 98%, or 99% sequence identity with the nucleotide sequence as shown in SEQ ID NO: 2, SEQ ID NO: 4, or SEQ ID NO: 22 calculated with the use of known algorithms for homology search, such as BLAST or FASTA (based on, for example, default (namely, initially set) parameters), and DNA encoding a protein comprising an amino acid sequence derived from the amino acid sequence of the protein encoded by any of the DNAs exemplified above by deletion, substitution, insertion, and/or addition of one or more, and preferably one or several amino acids, such as 1 to 10, preferably 1 to 7, more preferably 1 to 5, further preferably 1 to 3, and still further preferably 1 or 2 amino acids. DNA encoding a protein having activity of position-24-reducing enzyme is within the scope of such DNA.

These DNA is a homolog, analog, or variant of DNA comprising the nucleotide sequence as shown in SEQ ID NO: 2, SEQ ID NO: 4, or SEQ ID NO: 22. Such DNA can be obtained from leaves, roots, seeds, or other parts of a plant that generates cholesterols, such as plants of the family Solanaceae, such as potatoes (*Solanum tuberosum*), tomatoes (*Solanum lycopersicum*), and *Solanum glaucophyllum*, those of the family Scrophulariaceae, such as digitalis (*Digitalis purpurea*), and those of the family Labiatae, such as Ajuga reptans via hybridization, PCR amplification, or other techniques.

Under "stringent conditions," DNAs having high degrees of sequence identity hybridize to each other, and a person skilled in the art can adequately determine such conditions. For example, stringent conditions comprise "1×SSC, 0.1% SDS, 37° C.," more stringent (moderate-stringency) conditions comprise "0.5×SSC, 0.1% SDS, 42° C.," and further stringent (high-stringency) conditions comprise "0.1 to 0.2× SSC, 0.1% SDS, 65° C." Following hybridization, in addition, a step of washing may be carried out with, for example, 0.1×SSC and 0.1% SDS at 55° C. to 68° C., and the degree of stringency can then be increased. A 1×SSC buffer is composed of 150 mM sodium chloride and 15 mM sodium citrate and has a pH of 7.0.

Hybridization conditions and PCR procedures are described in, for example, F. M. Ausbel et al., Short Protocols in Molecular Biology, 3rd ed., John Wiley & Sons, 1995.

A further example of DNA encoding a position-24-reducing enzyme that can be used in the present invention is DNA comprising a sequence resulting from the degeneracy of the genetic code of the nucleotide sequence as shown in SEQ ID NO: 2, SEQ ID NO: 4, or SEQ ID NO: 22 (i.e., a degenerate sequence).

As described above, DNA according to the present invention encodes a protein having activity of position-24-reducing enzyme; specifically, any of the proteins (a) to (c) below:

(a) a protein comprising the amino acid sequence as shown in SEQ ID NO: 1, SEQ ID NO: 3, or SEQ ID NO: 21;

(b) a protein comprising an amino acid sequence derived from the amino acid sequence as shown in SEQ ID NO: 1, SEQ ID NO: 3, or SEQ ID NO: 21 by deletion, substitution, insertion, or addition of one or several amino acids and having activity of position-24-reducing enzyme; and (c) a protein comprising an amino acid sequence having 90% or higher sequence identity with the amino acid sequence as shown in SEQ ID NO: 1, SEQ ID NO: 3, or SEQ ID NO: 21 and having activity of position-24-reducing enzyme.

More specifically, DNA described above is selected from DNAs (d) to (g) below:

(d) DNA comprising the nucleotide sequence as shown in SEQ ID NO: 2, SEQ ID NO: 4, or SEQ ID NO: 22;

(e) DNA hybridizing under stringent conditions to DNA consisting of a nucleotide sequence complementary to DNA comprising the nucleotide sequence as shown in SEQ ID NO: 2, SEQ ID NO: 4, or SEQ ID NO: 22 and encoding a protein having activity of position-24-reducing enzyme;

(f) DNA comprising a nucleotide sequence having 90% or higher sequence identity with the nucleotide sequence as shown in SEQ ID NO: 2, SEQ ID NO: 4, or SEQ ID NO: 22 and encoding a protein having activity of position-24-reducing enzyme; and (g) DNA comprising a degenerate sequence of the nucleotide sequence as shown in SEQ ID NO: 2, SEQ ID NO: 4, or SEQ ID NO: 22.

3. Recombinant Vector

DNA according to the present invention is inserted expressibly into an adequate vector comprising a control sequence. The recombinant DNA thus obtained is a recombinant vector.

Any vectors that can be used in prokaryotic or eukaryotic cells can be used. Examples of vectors that can be used include microbial vectors of bacteria (e.g., *Escherichia, Pseudomonas, Bacillus,* and *Rhodococcus*), filamentous fungi (e.g., *Aspergillus, Neurospora, Fusarium, Trichoderma,* and *Penicillium*), *Basidiomycetes* (e.g., white-rot fungi), and yeast (e.g., *Saccharomyces, Pichia,* and *Candida*), plant cell vectors, and insect cell vectors.

Examples of bacterial vectors include pBR, pUC, pET, and pBluescript vectors. Examples of yeast vectors include, but are not limited to, pDR196, pYES-DEST 52, YIp5, YRp17, and YEp24 vectors. Examples of plant cell vectors include, but are not limited to, pGWB, pBiE12-GUS, pIG121-Hm, pBI121, pBiHyg-HSE, pB119, pBI101, pGV3850, and pABH-Hm1 vectors. Examples of insect cell vectors include, but are not limited to, pBM030, pBM034, and pBK283 vectors.

A constitutional element associated with gene expression, regulation, or secretion, such as a promoter, a terminator, an enhancer, the Shine-Dalgarno sequence, a ribosome-binding sequence, or a signal sequence, is incorporated into a vector used in the present invention, and a vector comprises a selection marker (e.g., a drug resistant gene or a reporter gene), according to need.

Examples of promoters include, but are not limited to, lac promoters, trp promoters, recA promoters, tac promoters, λPL promoters, T7 promoters, CaMV35S promoters, ADH1 promoters, GAL promoters, PHO5 promoters, PGK promoters, and GAPDH promoters.

Examples of drug resistant genes include kanamycin resistant genes, ampicillin resistant genes, and hygromycin resistant genes. Examples of reporter genes include lacZ genes, GFP genes, GUS genes, and luciferase genes. Examples of other selection markers include NPTII genes and dihydrofolate reductase genes.

It is preferable that a constitutional element associated with gene expression, regulation, or secretion be functionally incorporated into a recombinant vector in accordance with its properties. A person skilled in the art can adequately perform such procedure.

4. Method of Gene Suppression

The present invention provides a method for suppressing the expression of a gene encoding an enzyme that reduces position 24 of the steroid skeleton of a plant. Examples of methods for gene suppression that can be employed include the RNAi method via genetic recombination, the anti-sense method, the PTGS method involving the use of virus vectors, and direct introduction of small RNA. Also, methods for modifying the genomes, such as the zinc finger nuclease (ZFN) method, the tale nuclease (TALEN) method (Science, 333, 307, 2011), and Cre-loxP site-directed recombination, can be employed. Such methods occasionally involve the use of the sequence provided by the present invention as the site for direct introduction of a mutation. Alternatively, a sequence of a region adjacent to the sequence provided by the present invention may be identified based on sequence information, and the sequence of the adjacent region may be used, so as to delete the entire region of the gene encoding an enzyme that reduces position 24 of the steroid skeleton. In the present description, "suppression of gene expression" refers to reduction or elimination of RNA as a transcription product of a gene (DNA), a protein as a translation product, or enzymatic activity as a function of a protein. By suppressing the expression of a gene encoding an enzyme that reduces position 24 of the steroid skeleton, activity of the enzyme that reduces position 24 of the steroid skeleton of a plant is reduced or eliminated.

5. Selection of Gene Mutation, Polymorphic Mutant, and Gene Expression Mutation

The present invention provides a method for detecting the presence of a mutation in a gene encoding an enzyme that reduces position 24 of the steroid skeleton, a polymorphism such as a single nucleotide polymorphism (SNP), and a gene expression mutation in a plant. A mutant may be obtained by radiation, chemical treatment, UV irradiation, or spontaneous mutation.

The above method comprises steps of: isolating genomic DNA and/or RNA from mutant plants, various plant varieties, and improved plant varieties and synthesizing cDNA from RNA by reverse transcription; amplifying a gene fragment containing a gene encoding an enzyme that reduces position 24 of the steroid skeleton from DNA using the DNA amplification technique; and determining the presence of a mutation in the DNA. A commercially available kit (such as DNeasy or RNeasy, Qiagen) can be used for a method of DNA or RNA extraction. A commercially available kit (such as a SuperScript First-Strand System, Invitrogen) can also be used for a method of cDNA synthesis. For a method of gene fragment amplification using a DNA amplification technique, so-called PCR, LAMP, and other techniques can be employed. These techniques involve the use of polymerase so as to amplify (i.e., to increase the number of copies of) a specific DNA sequence through continuous polymerase reactions. This reaction can be employed instead of cloning, and this requires only information concerning the nucleic acid sequence. In order to perform DNA amplification, primers complementary to the DNA sequence to be amplified are designed. Subsequently, the designed primers are produced by automatic DNA synthesis. DNA amplification techniques are well known in the art, and a person skilled in the art can readily implement such techniques based on the teachings and instructions provided in the present description. Some PCR techniques (and related techniques) are described in, for example, U.S. Pat. Nos. 4,683,195, 4,683,202, 4,800,159, and 4,965,188 and "PCR Protocols: A guide to method and applications" edited by Innis et al.

In the step of determining the presence of a mutation or polymorphism in DNA, a detection method relying on homology between a mutant gene and a normal gene may be used. Examples of such method include the nucleotide sequencing (Applied Biosystems) and the TILLING method by which a mutant is detected using an enzyme that cleaves one member of a mismatched pair (Till et al., 2003, Genome Res 13: 524 to 530). The above method can be carried out by comparing the sequence data obtained by the above technique with the nucleotide sequence of a gene segment shown in SEQ ID NO: 2, 4, 7, or 22.

In the step of determining whether or not there is a difference in the amount of mRNA, cDNA may be subjected to quantitative PCR, such as RT-PCR or real-time PCR, using the primers produced based on the nucleotide sequence shown in SEQ ID NO: 2, 4, or 22. The results thereof may then be compared with the amount of cDNA obtained from the variety "Sassy," so that whether or not there is a difference in the amount of mRNA can be determined.

In a particularly preferable embodiment, the method for determining the presence of a mutation in the gene encoding an enzyme that reduces position 24 of the steroid skeleton defined as above is applied to material obtained from potatoes (*Solanum tuberosum*) belonging to the family Solanaceae or close relatives thereof (Example 9).

The genotypes and the phenotypes of the gene encoding an enzyme that reduces position 24 of the steroid skeleton of many wild-type potato plants or close relatives thereof remain unknown. By screening such wild-type plants, wild-type plants that have mutations in the biosynthetic genes and in which glycoalkaloid accumulation is undetectable or lower than that observed in cultivated plants or plants exhibiting lowered glycoalkaloid accumulation as a result of crossing can be selected.

Through the method of determining the presence of a mutation and/or a polymorphism, a mutation and/or a polymorphism in the gene encoding an enzyme that reduces position 24 of the steroid skeleton can be identified at the nucleotide level, and a plant comprising a mutation and/or a polymorphism in the gene encoding an enzyme that reduces position 24 of the steroid skeleton can be selected. The present invention encompasses a plant having a mutation and/or a polymorphism in the gene encoding an enzyme that reduces position 24 of the steroid skeleton that was obtained in the manner described above.

By determining that a mutation or polymorphism or a difference in the amount of mRNA exists, also, a plant in which the ability to express a gene encoding an enzyme that reduces position 24 of the steroid skeleton or the activity of an enzyme that reduces position 24 of the steroid skeleton is altered can be selected.

The ability to express a gene encoding an enzyme that reduces position 24 of the steroid skeleton or the activity of an enzyme that reduces position 24 of the steroid skeleton are suppressed by artificial mutagenesis, spontaneous mutagenesis, or genetic polymorphisms conserved in wild-type species. In this description, the expression "suppression of enzymatic activity" refers to reduction or elimination of the enzymatic activity. Suppression of activity of the enzyme that reduces position 24 of the steroid skeleton results in a situation in which normal functions of the enzyme that reduces position 24 of the skeleton structure are lowered or lost.

Examples of such gene mutation include deletion of all or part of the gene encoding an enzyme that reduces position 24 of the steroid skeleton, substitution of some nucleotides with other nucleotides, and insertion of nucleotides. An example of insertion of nucleotides is insertion of several tens to several hundreds of continuous nucleotides into an exon of a gene encoding an enzyme that reduces position 24 of the steroid skeleton. Examples of substitution of some nucleotides with other nucleotides include substitution of a conserved sequence at the 5' splice site in an intron and insertion of a sequence that generates a new exon in an intron. Such substitution would inhibit the occurrence of normal splicing. Plants having such gene mutations are within the scope of the present invention. Further, the present invention comprises selecting a plant having such gene mutation as a mother plant. In addition, such plant is subjected to crossing as a mother plant, and a progeny thereof is selected. Thus, a cultivated plant with a lowered risk of glycoalkaloid accumulation can be prepared. The term "cultivated plant" used herein refers to a plant variety that can be subjected to cultivation aimed at crop production.

Also, a plant in which activity of an enzyme that reduces position 24 of the steroid skeleton is suppressed can be obtained by artificially modifying a gene encoding an enzyme that reduces position 24 of the steroid skeleton. The present invention also includes a method for producing a plant that can be obtained by artificially modifying a gene encoding an enzyme that reduces position 24 of the steroid skeleton and a plant produced by such method. Modification of the activity of an enzyme that reduces position 24 of the steroid skeleton of a particular plant via mutation is modification of an existing variety of such plant. While a wild-type plant is within the scope of such existing varieties, a naturally-occurring wild-type plant that is not used for industrial applications is not considered to be an existing variety. For example, a modified plant resulting from mutation affecting the activity of an enzyme that reduces position 24 of the steroid skeleton comprises a sequence derived from a DNA sequence of the DWF1H gene as shown in SEQ ID NO: 22 by mutation so that A is substituted with T at position 427. As a result of such mutation, R (arginine) at position 143 is substituted with W (tryptophan) in the amino acid sequence (SEQ ID NO: 23) of the protein encoded by such gene. Another example of the modified plant resulting from mutation affecting the activity of an enzyme that reduces position 24 of the steroid skeleton is a plant with a sequence that lacks the entire allele S as shown in SEQ ID NO: 2. An existing variety refers to any of the plant varieties that are produced when the activity of an enzyme in such plant that reduces position 24 of the steroid skeleton is modified. That is, plant varieties produced by an artificial procedure, such as crossing or genetic engineering, are within the scope thereof. In the present invention, a plant is not required to exhibit enzymatic activity that is lower than that of every existing plant variety in order to fall under the category of "plant(s) in which the activity of an enzyme that reduces position 24 of the steroid skeleton is suppressed." As long as the activity of a plant is suppressed in comparison with that of a particular existing variety, such plant would fall under the category of "plant(s) in which the activity of an enzyme that reduces position 24 of the steroid skeleton is suppressed." A plant with the activity that is naturally suppressed via mutation without artificial procedure is within the scope of "plant(s) in which the activity of an enzyme that reduces position 24 of the steroid skeleton is suppressed." According to the method of the present invention, a plant in which the activity is naturally suppressed can be selected and established as a novel plant variety. When a particular existing plant variety is subjected to mutagenesis to prepare a plant in which activity of an enzyme that reduces position 24 of the steroid skeleton is suppressed, a control plant may be an existing variety that is the same as or different from the plant variety subjected to mutagenesis. Alternatively, a gene encoding an enzyme that reduces position 24 of the steroid skeleton selected from nature or produced via mutagenesis may be subjected to crossing with a gene of a plant having a mutation or polymorphism, so that the mutation of the gene encoding an enzyme that reduces position 24 of the steroid skeleton is fixed, and a novel plant variety with suppressed ability to express a gene encoding an enzyme that reduces position 24 of the steroid skeleton or activity of an enzyme that reduces position 24 of the steroid skeleton can be obtained.

When the plant is a potato (*Solanum tuberosum*), examples of existing varieties include "Cynthia," "Sassy" (sold by Japan Agribio Company, Limited), "Cheme," "Irish Cobbler (i.e., Danshaku)," "May Queen," and "Sayaka (Ministry of Agriculture, Forestry and Fisheries registration number: Norin No. 36)." A plant in which the ability to express a gene encoding an enzyme that reduces position 24 of the steroid skeleton or activity of an enzyme that reduces position 24 of the steroid skeleton is suppressed in comparison with an existing variety encompasses a plant in which the ability to express a gene encoding an enzyme that reduces position 24 of the steroid skeleton is lowered in comparison with an existing variety. Also, a plant in which the activity of an enzyme that reduces position 24 of the steroid skeleton is lowered in comparison with an existing variety is within the scope of the plant as described above. A plant in which the ability to express a gene encoding an enzyme that reduces position 24 of the steroid skeleton or activity of an enzyme that reduces position 24 of the steroid skeleton is suppressed in comparison with an existing variety is within the scope of the present invention.

In a plant in which the activity of an enzyme that reduces position 24 of the steroid skeleton is lowered, the amount of an enzyme that reduces position 24 of the steroid skeleton synthesized is low, or such enzyme cannot be synthesized. Also, the content of the enzyme that reduces position 24 of the steroid skeleton is low in the plant, or such enzyme is absent in the plant. Alternatively, the activity of the enzyme that reduces position 24 of the steroid skeleton is low or eliminated. Accordingly, the plant has low glycoalkaloid content or lacks glycoalkaloids. In the case of a potato, for example, a glycoalkaloid such as chaconine or solanine is not synthesized, and thus the amount of a glycoalkaloid such as chaconine or solanine synthesized or existing in the potato tubers is low. In the case of a tomato, a glycoalkaloid such as tomatine is not synthesized, and thus the amount of a glycoalkaloid such as tomatine synthesized or existing in tomato fruit is low.

In a potato in which the activity of the enzyme that reduces position 24 of the steroid skeleton is low or lost, a glycoalkaloid such as chaconine or solanine is not synthesized in tubers, or the amount of a glycoalkaloid such as chaconine or solanine synthesized in tubers is lower than that in the existing variety described above. In such a case, also, the amount of a glycoalkaloid such as chaconine or solanine existing in tubers is low.

With the use of a plant having a mutation in a gene encoding an enzyme that reduces position 24 of the steroid skeleton (i.e., a mutant plant prepared by artificial modification of a gene encoding an enzyme that reduces position 24 of the steroid skeleton or a wild-type plant selected via screening) as a mother plant, a cultivated plant accumulating a reduced amount of or no glycoalkaloid and exhibiting good taste and cultivation properties can be produced. In the present invention, a plant in which "glycoalkaloid accumulation is reduced" is a cultivated plant in which the amount of glycoalkaloids accumulated or the rate of glycoalkaloid accumulation is lower than that of the mother plant used for the production thereof. In the present invention, a plant in which "glycoalkaloid accumulation is lost" is a cultivated plant in which the amount of glycoalkaloids becomes lower than the detection limit under conditions in which an existing plant variety would accumulate glycoalkaloids. In the present invention, glycoalkaloid accumulation is lowered or lost in the "cultivated plant in which a risk of glycoalkaloid accumulation is lowered."

6. Production of Cultivated Plant in which Glycoalkaloid Accumulation is Lowered or Lost Via Crossing With the use of the variant obtained or the wild-type plant selected above as a mother plant, a cultivated plant in which glycoalkaloid accumulation is lowered or lost can be produced. If the mother plant is a variant obtained from a cultivated plant, it is considered to be effective to subject such variant to crossing or a variant having mutations at different sites of the same target gene to crossing, in order to fix the mutation of interest at an early stage. Concerning crossing with potatoes or close relatives thereof, damage such as classic self-incompatibility or incompatibility according to the Endosperm Balance Number (EBN) hypothesis has been known. Such plants may be subjected to processing, such as direct pollination of ovules, ovule culture, reciprocal crossing, or somatic cell fusion, so that crossing or processing equivalent thereto can be realized. Such processing may be implemented with reference to "*Jagaimo Jiten* (Dictionary of Potatoes)," 2012, edited by the Japan Root and Tuber Crops Development Association Inc. Foundation, Zenkoku Noson Kyoiku Kyokai, Co., Ltd. or "Handbook of Potato Production, Improvement, and Postharvest Management," 2006, edited by Gopal and Paul Khurana, pp. 77-108, Haworth Press Inc. When a wild-type plant is a parent plant having a gene with a mutation, the resulting plant is designated as a cultivated plant and subjected to backcrossing. Thus, a gene with a mutation can be introduced while maintaining good taste and excellent properties of cultivated plants. Also, the site of mutation in the gene may be analyzed at the nucleotide sequence level, so that a mutation-related gene marker can be obtained. With reference to the genomic information on, for example, the potato genome sequence (Nature, 2011; 475: 189-95) reported in 2011, in addition, a plurality of gene markers located in the vicinity of the gene of interest can be obtained, and progeny plants into which sites of mutation of interest have been selectively introduced can be efficiently selected. If particular markers are obtained in regions that cover the entire genome beyond regions in the vicinity of the gene of interest, a necessary portion (genetic region) can be selectively transferred. When there is genetic distance between a marker and a gene to be introduced (i.e., a trait), the marker may have a certain probability of differing from the trait. This requires a trait to be tested. However, genetic mutation discovered in the present invention is consistent with the relevant trait, and it is not necessary to test such trait. This enables conclusive testing of the seeds subjected crossing when the seeds germinate and DNAs are obtained. Testing involving the use of a DNA marker can be carried out with reference to, for example, "*Genomu reberu no iden kaiseki* (Genome-level genetic analysis) MAP and QTL," Yasuo Ukai, 2001, University of Tokyo Press. For example, the presence of the DNA markers can be determined with the use of polynucleotides, such as primers. A gene mutation test involving the use of a DNA marker can be carried out in combination with a trait test via glycoalkaloid analysis. When a cultivated plant is identified, in particular, it is preferable that reduction or elimination of glycoalkaloid accumulation be confirmed via analysis at each stage from plant growth to potato tuber storage.

EXAMPLES

Hereafter, the present invention is described in greater detail with reference to the examples, although the present invention is not limited thereto.

Example 1

Extraction of Gene of Position-24-reducing Enzyme from cDNA Sequence of Potato Sprouts Potato sprouts are known to accumulate a very large amount of glycoalkaloids. While a glycoalkaloid biosynthetic pathway remains unknown, cholesterol is considered to serve as a starting material. Thus, the potato sprouts were considered to be the organs capable of cholesterol synthesis in plants and the excellent gene source for cholesterol biosynthesis.

Following harvesting and storage for 3 months or longer, potatoes after a rest period were allowed to stand in the dark at 20° C. and to sprout for about 2 weeks. The resulting sprouts were grounded with liquid nitrogen and total RNA was extracted with the use of RNeasy (Qiagen). cDNA was synthesized from 2 μg of RNA via reverse transcription with the use of a primer comprising a T7 promoter sequence added thereto. With the use of DNA polymerase and T7 RNA polymerase, the resulting fragment was amplified as RNA, and reverse transcription was carried out again to synthesize cDNA. With the use of an adaptor for GS FLX analysis, cDNA double-strands were synthesized therewith. After the synthesized double strands were physically cleaved to a fragment of several hundreds of base pairs, another adaptor for GS FLX analysis was ligated thereto to recover single-stranded DNA. With the use of the resultant as a template, approximately 150,000 expressed gene sequences were analyzed using the Genome Sequencer FLX System (assigned to Takara Bio, Inc.). As a result, 54 gene fragments having high homology to the DWF1 gene of an enzyme that reduces methylene 24 of cholesterol in *Arabidopsis thaliana* (i.e., StDWF1 exhibiting amino acid sequence identity of 78.0% for 564 amino acid residues in the full-length sequence obtained in Example 2) and 80 gene fragments having lower sequence homology (i.e., StDWF1 homologs: StDWF1H, exhibiting amino acid sequence identity of 75.5% for 556 amino acids relative to the full-length amino acid sequence obtained in Example 2) were discovered.

Example 2

Identification of StDWF1H Gene

With the use of the gene fragment mentioned above, primers: U931 (caccATGTCGGATGCTAAGGCCC (SEQ ID NO: 8), "cacc" is an additional sequence used for cloning into a vector) and U932 (TCAATTCGCAGGTTCATCAG (SEQ ID NO: 9)) were synthesized in order to obtain a full-length sequence of StDWF1H based on the sequence data SGN-U268686 in the Sol Genomics Network (http://solgenomics.net/index.pl). Primers: U957 (caccATGACAGATGTTCAGGCTCC (SEQ ID NO: 10), "cacc" is an additional sequence used for cloning into a vector) and U958 (TCAATCTTCAGGCTCATCAACT (SEQ ID NO: 11)) were synthesized in order to obtain a full-length sequence of StDWF1 based on the sequence data TC214162 of the DFCI Potato Gene Index (http://compbio.dfci.harvard.edu/tgi/plant.html). Total cDNA was synthesized from total RNA of Example 1 and applied to a SuperScript First-Strand System (Invitrogen). This cDNA was used as a template to amplify a gene by PCR at an annealing temperature of 55° C. (30 cycles, with the use of PrimeSTAR HS DNA Polymerase, Takara Bio, Inc.). The resultant was cloned into the pENTR™/D-TOPO Entry vector (Invitrogen). Polynucleotide sequences of the obtained 8 independent clones were determined. The determined sequences are as shown in SEQ ID NO: 2 and SEQ ID NO: 6, and polypeptide sequences deduced based thereon are as shown in SEQ ID NO: 1 and SEQ ID NO: 5. These vectors were designated as pTOPO-PSStDWF1H and pTOPO-PSStDWF1. FIG. 1 shows the alignments demonstrating the results of homology analysis between StDWF1H and StDWF1, and amino acid sequence identity was very high (i.e., 80.0% for 562 amino acids). A degree of homology of StDWF1H with a human gene that is known as a position-24-reducing enzyme gene (i.e., the DHCR24 gene, Am. J, Hum, Genet., 2001, 69, 685-94) was 40.3% in terms of amino acid sequence identity for 533 amino acids, and that of StDWF1 was 39.0% for 533 amino acids. A degree of homology between DHCR24 and DWF1 was 39.8% for 522 amino acids. The degree of homology above was as low as about 40%, and it was difficult to predict functions on the basis of the results of gene homology analysis at this point.

Further, the full-length gene sequence of the relevant potato was identified to be SGN-U578468 on the basis of the sequence information in the Sol Genomics Network (http://solgenomics.net/index.pl) and the identified sequence was obtained. The identified sequence is as shown in SEQ ID NO: 4, and a polypeptide sequence deduced based thereon is as shown in SEQ ID NO: 3.

These sequences were compared with the amino acid sequences of the genes of the enzymes (DWF1) that reduce methylene at position 24 of cotton, *Gossypium hirsutum* (Genbank Accession Number AAM47602.1), rice, *Orysa sativa*, (Genbank Accession Number AAP53615), pea, *Pisum sativum*, LKB (Genbank Accession Number AAK15493), and *Arabidopsis thaliana* that are described as homologous to the gene of position-24-reducing enzyme derived from human in JP 2004-535960 A (the title of the invention: Cholesterol-producing yeast strains and uses thereof), and a molecular phylogenetic tree was prepared by the Bootstrap method using CLUSTALX 2.0 (Larkin et al., 2007, Clustal W and Clustal X, Version 2.0, Bioinformatics, 23: 2947-2948) (FIG. 2). As a result, StDWF1H and SlDWF1H were found to be classified into a cluster different from the cluster of an enzyme (DWF1) that reduces methylene at position 24 of cholesterol, and the relationship thereof with a human DHCR24 gene of the position-24-reducing enzyme was found to be distant from the viewpoint of evolution.

Example 3

Identification of Genomic Gene of StDWF1H Gene

Genomic DNA was extracted from "Sassy" using DNeasy (Qiagen). PCR was carried out using the same primers as those used in Example 1 (U957: caccATGACAGATGTTCAGGCTCC (SEQ ID NO: 10) and U958: TCAATCTTCAGGCTCATCAACT (SEQ ID NO: 11)) to determine the nucleotide sequence of the full-length genomic DNA (SEQ ID NO: 7). The sequence was found to comprise an intron.

The genomic sequence of the potato gene was reported recently (Xu et al., Nature, 2011, 475: 189-197). The genomic sequence is disclosed on the website of the Potato Genome Sequencing Consortium Data Release (http://potatogenomics.plantbiology.msu.edu/index.html). On the basis of this sequence, the genomic gene of the StDWF1H gene can be determined. The genomic sequence of the potato gene is also disclosed on the Sol Genomics Network (http://solgenomics.net/index.pl), and the sequence is reported to comprise an intron. However, there is no report concerning functions on these websites.

Example 4

Figure 3:
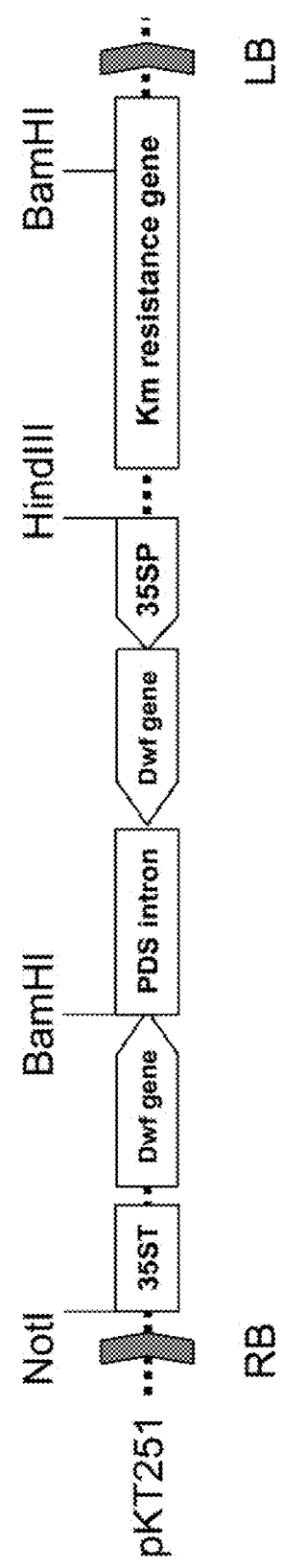
FIG. 3 shows the construction of a vector for DWF1H gene suppression, showing the internal constructions of the right border (RB) and left border (LB) and the restriction enzyme sites of T-DNA, which is the gene to be introduced.

Vector Construction for Production of Transformant in which StDWF1H Gene is Suppressed As to the method for suppressing the above gene by transformation, a reverse complementary gene fragment configured to be driven by a strong promoter was expressed (generally referred to as the RNAi method in plants) (Chuang and Meyerowitz, Proc. Natl. Acad. Sci, U.S.A., 97, 4985 to 90, 2000; Wesley et al., Plant J., 27, 581 to 90, 2001). The full-length cDNA obtained in Example 1 was subjected to PCR with the use of the primers (U952: GAGCTCTAGACCCTAGGAGGAAGATCCAG (SEQ ID NO: 12) and U953: GGATCCATATGCGTTTCTCATTCCAACAACA (SEQ ID NO: 13)) at an annealing temperature of 55° C. (30 cycles, with the use of ExTaq DNA Polymerase, Takara Bio Inc.) to amplify the gene. The resultant was cloned into the pCR4-TOPO vector (Invitrogen) to obtain a gene fragment. Based on the binary vector pKT11 (JP 2001-161373 A), a vector pKT251 for plant transformation was prepared by ligating a cauliflower mosaic virus 35S RNA promoter, the above gene fragment (in the forward direction), the third intron of the *Arabidopsis thaliana* phytoene desaturase gene (AT4g14210), the above gene fragment (in the reverse direction), and a cauliflower mosaic virus 35S RNA terminator in this order (FIG. 3).

Example 5

Production of Transformed Potato Plant

The vector prepared in Example 4 was introduced into the *Agrobacterium tumefaciens* GV3110 strain by the electroporation method (edited by Gelvin and Schilperoor, Plant Molecular Biology Manual, C2, 1 to 32, 1994, Kluwer Academic Publishers). The *Agrobacterium tumefaciens* GV3110 strain containing the vector was subjected to shaking culture at 28° C. for 12 hours in a YEB liquid medium (5 g/l beef extract, 1 g/l yeast extract, 5 g/l peptone, 5 g/l sucrose, and 2 mM magnesium sulfate (pH 7.2)) containing 50 ppm kanamycin. The resulting culture solution (1.5 ml) was centrifuged at 10,000 rpm for 3 minutes to collect the bacteria, followed by washing in 1 ml of an LB medium for removal of kanamycin. Further, centrifugation was performed at 10,000 rpm for 3 minutes to collect the bacteria, the collected bacteria were resuspended in 1.5 ml of an MS medium containing 3% sucrose (Murashige and Skoog, Physiol. Plant., 15, 473 to 497, 1962), and the resultant was designated as a bacterial solution for infection.

Potato transformation was carried out according to the literature (Monma, 1990, *Shokubutsu Soshiki Baiyo* (Plant Tissue Culture) 7: 57 to 63). Microtubers obtained from the potato variety "Sassy" (Japan Agribio Co., Ltd.) were sliced to a thickness of 2 to 3 mm and provided as materials for *Agrobacterium* infection. The resulting slices were immersed in the aforementioned Agrobacterial solution and placed on sterilized filter paper so as to remove excess Agrobacteria. The slices were then placed on an MS medium (containing 1 ppm zeatin, 0.1 ppm IAA, 100 µM acetosyringone, and 0.8% agar) in a petri dish. The slices were then cultured under the conditions of 25° C., illumination for 16 hours (at a photon flux density of 32 µE/m$^2$s)/non-illumination for 8 hours for 3 days. Subsequently, the slices were cultured in a medium containing 250 ppm carbenicillin in place of acetosyringone for 1 week. Thereafter, the slices were transferred onto a medium containing 50 ppm kanamycin, followed by subculture at 2-week intervals. During subculture, adventitious buds were formed and shoots grew. The elongated shoots were placed on an MS medium containing 250 ppm carbenicillin and 100 ppm kanamycin without plant growth regulators. A plant having a kanamycin-resistant gene as an exogenous gene was detected from among kanamycin-resistant, grown plants by subjecting the rooted shoots to PCR (conditions: 95° C. for 5 minutes, 30 cycles of 95° C. for 30 seconds, 55° C. for 30 seconds, and 72° C. for 1 minute, and 72° C. for 10 minutes). Thus, the regenerated plant was confirmed to be a transformant. As the primers for specifically amplifying the kanamycin-resistant gene sequence, the following primers were used: TAAAGCACGAGGAAGCGGT (SEQ ID NO: 14) and GCACAACAGACAATCGGCT (SEQ ID NO: 15). Thus, 39 lines of transformed potato plants into which the vector pKT251 had been introduced were obtained.

Example 6

Analysis of Glycoalkaloid Content and DWF1H Gene Expression in Plant Transformant The in vitro stems of the 39 plants obtained in Example 5 were elongated for 1 month after subculture. Thereafter, 2 to 4 of the elongated parts were put together to bring the amount thereof to about 100 mg, and the glycoalkaloid content therein was measured by the following method employing liquid chromatography with a column for alkali-resistant reversed-phase chromatography (JP 2011-27429 A). To the sample, 990 µl of 0.1% formic acid in 80% MeOH aq. and, as an internal standard, 10 µg/10 µl brassinolide (Brassino Co., Ltd.) were added, followed by pulverization using a mixer mill (1/25 sec, 10 min, 4° C.). The pulverized products thus obtained were centrifuged at 10,000 rpm for 5 minutes at 4° C. and then subjected to alcohol precipitation. The supernatant (25 µl) was fractionated, 475 µl of 0.1% aqueous formic acid was added, the mixture was filtered with the use of a multiscreen sorbinate (Millipore), and analysis was then carried out using LC-MS (LCMS-2010EV, Shimadzu Corporation; or Alliance e2795 Q-micro, Waters). LC conditions were analyzed via separation using a column XBridge™ Shield RP18-5 (diameter of 2.1×150 mm, Waters) and the mobile phase (a mobile phase A: 10 mM aqueous ammonium hydrogen carbonate (pH 10) and a mobile phase B:acetonitrile (40:60)) under the isocratic conditions (column oven: 40° C.). Quantification was carried out using the standard products (chaconine and solanine, Sigma-Aldrich).

Figure 4:
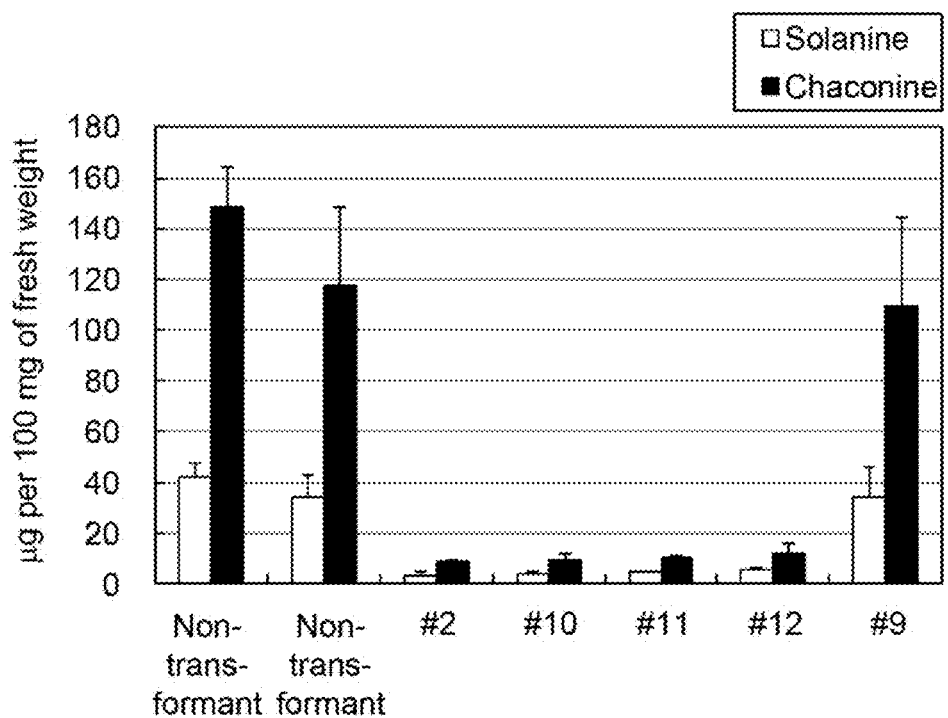
FIG. 4 shows the glycoalkaloid content in the in vitro stems of potato transformants. Each error bar indicates the standard deviation.

The in vitro stems of the 39 plants were analyzed twice. As a result, the amounts of glycoalkaloids accumulated in 4 lines (#2, #10, #11, and #12) were found to be low with good reproducibility. The in vitro stems (about 200 mg) were collected from 4 lines in which the amount of glycoalkaloids accumulated was low, a line (#9) in which the amount of glycoalkaloids accumulated was not low, and 2 control plants into which the gene was not introduced. These in vitro stems were pulverized with liquid nitrogen, a half thereof was subjected to measurement of the glycoalkaloid content, and the other half was subjected to measurement of mRNA. The amount of glycoalkaloids accumulated in the 4 lines in which the amount of glycoalkaloids accumulated was low was considerably lower than that observed in the 2 non-transformed plants or the line in which the amount of glycoalkaloids accumulated was not low (FIG. 4). Total RNA was extracted from each plant using RNeasy (Qiagen), and total cDNA was synthesized using a SuperScript First-Strand System (Invitrogen). As a result of RT-PCR (PCR conditions: 95° C. for 5 minutes and 20 cycles of 95° C. for 30 seconds, 55° C. for 30 seconds, and 72° C. for 3 minutes) using the primers (U1005: CTCTGCTCAAAGCCACA-CAA (SEQ ID NO: 16) and U932: TCAATTCGCAGGT-TCATCAG (SEQ ID NO: 17)), it was found that mRNA expression of the DWF1H gene was extremely low or unobservable in 5 plants in which the amount of glycoalkaloids accumulated was low (FIG. 5). As a result, suppression of the DWF1H gene expression was found to result in an extremely reduced amount of glycoalkaloids accumulated, and the DWF1H gene was found to encode a glycoalkaloid biosynthetic enzyme that encodes an enzyme reducing position 24 of the steroid skeleton.

Example 7

Preparation of Tuber from Transformed Plant of Low-glycoalkaloid Line

The in vitro plants of these 4 low-glycoalkaloid lines were amplified together with non-transformed plants, and 3 plants from each line were habituated to commercially available culture soil for vegetables, and the plants were then cultivated in a biohazard greenhouse according to a general method to obtain tubers. Each of these 4 lines (#2, #10, #11, and #12) grew in a manner equivalent to the non-transformed plants, and equivalent tubers were obtained therefrom (Table 1).

TABLE 1

Yield of tubers of low-glycoalkaloid lines

| Line No. | Number of tubers | S.D. | Average weight per tuber (g) | Total weight of plant (g) | S.D. |
|---|---|---|---|---|---|
| Non-transformant | 5.0 | 3.6 | 43.0 | 102.0 | 16.1 |
| #2 | 4.0 | 1.0 | 31.1 | 124.4 | 50.6 |
| #10 | 3.7 | 2.1 | 48.0 | 127.8 | 48.9 |
| #11 | 3.3 | 0.6 | 42.3 | 140.2 | 19.8 |
| #12 | 2.7 | 1.5 | 76.3 | 144.4 | 3.6 |

Figure 6:
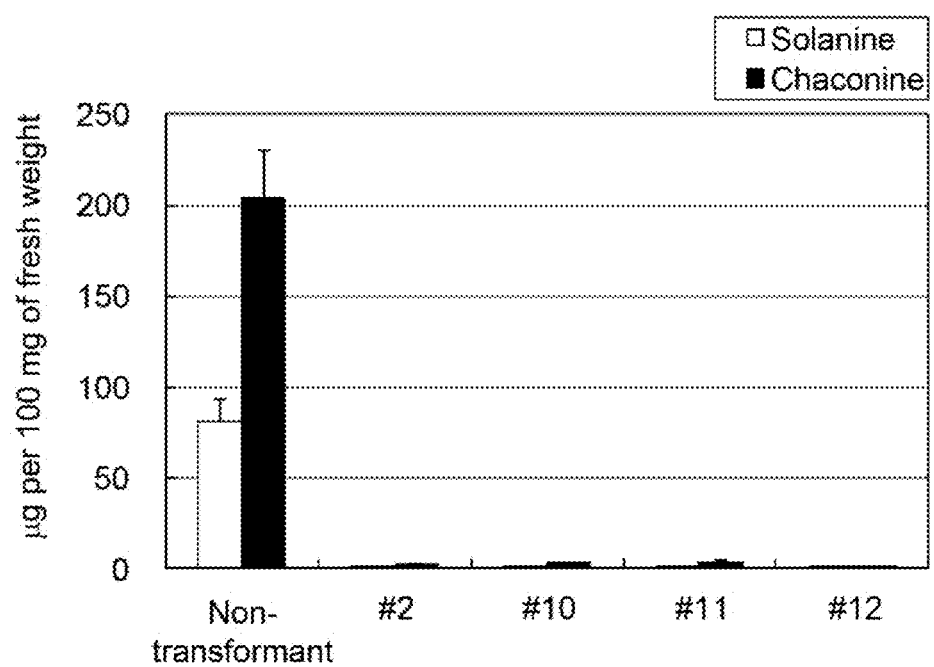
FIG. 6 shows the glycoalkaloid content in the tuber epidermis of potato transformants. Each error bar indicates the standard deviation.

Further, the epidermis of the center part of each of the 3 harvested tubers was peeled with a thickness of about 1 mm, and the glycoalkaloid content was analyzed in the same manner. As a result, surprisingly, the glycoalkaloid content in the tubers was found to be extremely low (FIG. 6). These 4 transformed lines grew normally, and no traits such as dwarfism observed in *Arabidopsis thaliana* containing mutations in the DWF1 gene were observed. This indicates that there is a low degree of association between the DWF1H gene and the biosynthetic pathways of brassinolide, which is a plant hormone exhibiting a high degree of association with dwarfism, and that the DWF1H gene is a gene encoding an enzyme that reduces position 24 of the steroid skeleton exhibiting a high degree of association with the biosynthetic pathway of glycoalkaloids.

Example 8

Production of Transformed Tomato Plant

Figure 7:
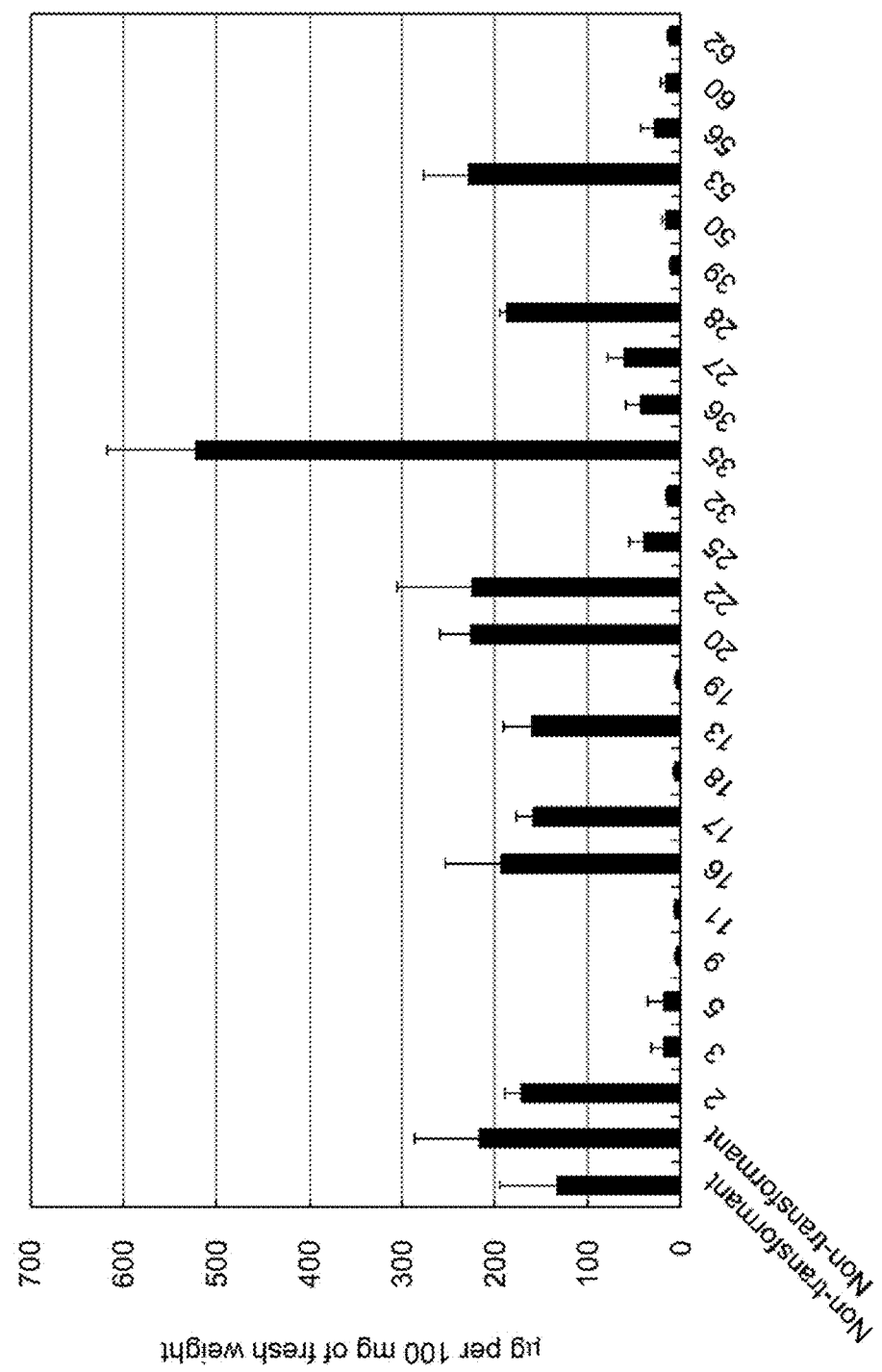
FIG. 7 shows the glycoalkaloid content in young leaves of tomato transformants. Each error bar indicates the standard deviation.

Tomato transformation was performed according to the literature (Sun et al., 2006, Plant Cell Physiol., 47: 426-431). The *Agrobacterium tumefaciens* AGLO strain containing the vector pKT251 prepared in (Example 4) was cultured to give a bacterial solution for infection. Sections of 5 mm or smaller taken from the cotyledons of the experimental line of tomatoes (*Solanum lycopersicum*) called "Micro-Tom" obtained by sterile seeding were immersed in the aforementioned *Agrobacterium* suspension for 10 minutes to allow infection to take place. The leaves were then placed on sterilized filter paper to remove excess Agrobacteria. The leaves were placed on a coculture MS medium (containing 1.5 mg/l zeatin, 40 μM acetosyringone, and 0.3% Gelrite®) (Murashige and Skoog, Physiol. Plant., 15, 473 to 497, 1962) in a petri dish. The petri dish was placed in a dark place and culture was performed at 25° C. for 3 days. The sections were subjected to subculture at 2-week intervals in a selective MS medium 1 (containing 1.5 mg/l zeatin, 100 mg/l kanamycin, 375 mg/l augmentin, and 0.3% Gelrite®) under the conditions of illumination for 16 hours (at a photon flux density: 32 μE/m$^2$s)/non-illumination for 8 hours at 25° C. During subculture, adventitious buds were formed and shoots grew. In order to further elongate the shoots, the shoots were transplanted to a selective MS medium 2 (containing 1.0 mg/l zeatin, 100 mg/l kanamycin, 375 mg/l augmentin, and 0.3% Gelrite®). The elongated shoots were allowed to root in a selective ½ concentration MS medium (containing 100 mg/l kanamycin, 375 mg/l augmentin, and 0.3% Gelrite®). A plant having a kanamycin-resistant gene as an exogenous gene was detected from among kanamycin-resistant, grown plants by subjecting the shoots to PCR using primers that specifically amplify the sequence of the kanamycin-resistant gene. Thus, the regenerated plant was confirmed to be a transformant. The transformed tomato plants (24 lines) into which the vector pKT251 had been introduced were obtained. These 24 plants were habituated in a greenhouse and cultivated for about 1 month. From each of 3 newly developed young leaves, about 100 mg was weighed out, and the glycoalkaloid content (i.e., the α tomatine content; the standard α tomatine product of Sigma Aldrich was used) was measured by the method employed in Example 6 in a manner similar to that for potatoes, except that analysis was performed with a ratio of mobile phase A to mobile phase B of 60:40. Among the 24 plants, tomatine content was remarkably low in 12 plants, which was ⅕ or less (i.e., 34 μg or less) of 174 μg per 100 mg fresh weight, which was the average of control plants (FIG. 7). These transformed lines grew normally.

Example 9

Production of Potato Containing Mutations in StDWF1H Gene

Figure 8:
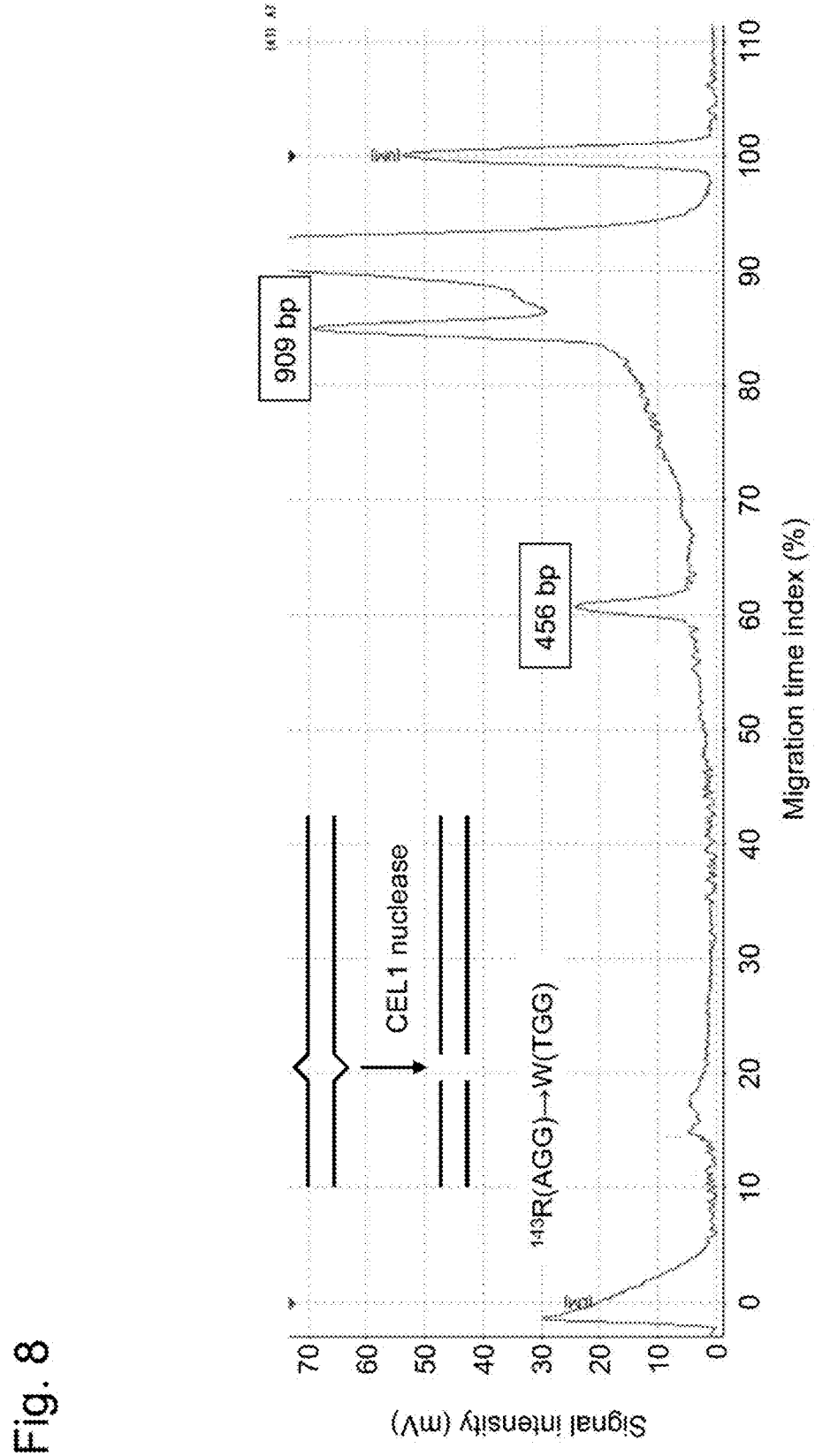
FIG. 8 shows the results of MultiNA analysis of the mutant M1 of the potato StDWF1H gene by the Tilling method. The two peaks indicate two fragments obtained by cleaving the sites of mutation with CEL1 nuclease and the lengths thereof.

Self-propagating seeds of the potato variety "Hokkaikogane" were subjected to mutation treatment by means of particle beam irradiation (an NIRS-HIMAC irradiation apparatus; Radiation Research 154, 485-496, 2000), a 90 to 470 Gy neon ion beam (30 kev/μm), and a 20 to 80 Gy iron ion beam (185 kev/μm). The seeds were immersed in a solution containing 2,000 ppm of gibberellin (Kyowa Hakko Kirin Co., Ltd.) for 2 days, and the resultants were sowed in commercially available culture soil. Culture was conducted for a photoperiod of 14 hours at a temperature of 23° C., and the lengths thereof reached approximately 3 cm and 4 foliage leaves developed approximately 20 days later. The shoot apex was then cut back to a point just above the lowest foliage leaf. Approximately 2 weeks thereafter, a lateral bud extended from the cut-back node, and DNA was extracted from the leaf developed from the lateral bud. Leaves of the 4 plants were collectively used as a single sample, 450 μl of an extraction liquid (0.1 M Tris-HCl, pH 8.5, 40 mM EDTA, 0.6 M NaCl) was added thereto, and the resultant was pulverized using zirconia beads and a mixer mill (Retsch) (oscillation cycle ⅕ sec, 5 min). A Proteinase K solution (10 mg/ml) was added in an amount of 10 μl, and treatment was then carried out at 55° C. for 20 minutes. Thereafter, 160 μl of 5 M potassium acetate was added and centrifugation was carried out at 15,000 rpm for 5 minutes. The supernatant (100 μl) was precipitated in the equivalent amount of isopropanol, and the resultant was dissolved in 100 μl of a TE solution (10 mM Tris-HCl, pH 8.0, 1 mM EDTA) to prepare pooled DNA samples. Mutation was detected by the Tilling method (Nature Protocol 1, 2465-2477). The StDWF1H gene of Hokkaikogane had a sequence as shown in SEQ ID NO: 22 (allele K) comprising a nucleotide sequence different from the nucleotide sequence as shown in SEQ ID NO: 2 (allele S) by 23 bases. An amino acid sequence deduced based on the above nucleotide sequence is shown in SEQ ID NO: 21. In order to detect mutation, it is necessary to amplify SEQ ID NO: 2 separately from SEQ ID NO: 22. The first exon of the DWF1H gene as shown in SEQ ID NO: 2 was amplified using the primers: U1015: CTCTGCTCAAAGCCACACAA (SEQ ID NO: 18) and U1016: CCGTTAAGAGTTGCCAAAAACC (SEQ ID NO: 19), and the first exon of the DWF1H gene as shown in SEQ ID NO: 22 was amplified using the primers: U1015 and U1010: CAAATTTTGAATGGAGGGGTAT (SEQ ID NO: 20). DNA was amplified by PCR (conditions: 95° C. for 5 minutes, 30 cycles of 95° C. for 30 seconds, 55° C. for 30 seconds, and 72° C. for 1 minute, and 72° C. for 5 minutes), denatured at 98° C. for 2 minutes, and then reassociated. Thereafter, a solution containing CEL1 nuclease (Nature Protocol 1, 2465-2477) was added, and treatment was carried out at 45° C. for 15 minutes. The DNA product was subjected to electrophoresis on 8% acrylamide gel or electrophoresis with the use of MultiNA (Shimadzu Corporation) and the DNA-1000 Kit (Shimadzu Corporation), and plants comprising mutation were detected as bands that had newly emerged. From the pooled DNA samples in which mutation had been detected, DNA was individually extracted again, and mutants were identified by the Tilling method. A plant that had undergone point mutation was subjected to PCR using the primers U1015 and U1010, and the amplified product was then subjected to cloning using the TOPO TA Cloning Kit for Sequencing (Invitrogen). Further, nucleotide sequences were determined using ABI310 (Applied Biosystems) and the sites of mutation were identified. As a result of sowing of 12,495 seeds and screening of the grown 3,617 plants, 11 mutants were obtained. The sites of mutation in each plant are as shown in Table 1. FIG. 8 shows the results of electrophoresis of the M1 mutant by the Tilling method. Genetic mutation causes a mismatch pair with the normal allele, and the sequence is cleaved with CEL1 nuclease. Thus, two fragments (456 bp and 909 bp fragments) were obtained.

TABLE 2

| No. | Ion for mutation and intensity thereof | Site of mutation |
| --- | --- | --- |
| M1 | 250 Gy of Ne | "A" at position 427 of DNA of allele K with "T" (mutation of R with R at amino acid 143) |
| M2 | 40 Gy of Fe | Deletion of entire allele S |
| M3 | 40 Gy of Fe | Deletion of entire allele S |
| M4 | 40 Gy of Fe | Deletion of entire allele S |
| M5 | 60 Gy of Fe | Deletion of entire allele S |
| M6 | 60 Gy of Fe | Deletion of entire allele S |
| M7 | 60 Gy of Fe | Deletion of entire allele S |
| M8 | 250 Gy of Ne | Deletion of entire allele S |
| M9 | 250 Gy of Ne | Deletion of entire allele S |
| M10 | 250 Gy of Ne | Deletion of entire allele S |
| M11 | 280 Gy of Ne | Deletion of entire allele S |

INDUSTRIAL APPLICABILITY

The present invention can provide a plant belonging to the family Solanaceae, such as a potato, that does not accumulate glycoalkaloids therein.

SEQUENCE LISTING FREE TEXT

SEQ ID NOs: 8 to 20: Primers

All publications, patents, and patent applications cited herein are incorporated herein by reference in their entirety.

The invention claimed is:

1. A method for producing a plant belonging to the family Solanaceae which has no traits of dwarfism and has a reduced risk for accumulation of glycoalkaloids, comprising suppressing the expression of a gene encoding an enzyme that reduces a double bond between C24 and C25 of the steroid skeleton by artificial procedure, the gene consisting of any one of DNAs (a) to (c) below:
   (a) DNA consisting of the nucleotide sequence as shown in SEQ ID NO: 2, 4 or 22;
   (b) DNA consisting of a nucleotide sequence having 95% or higher sequence identity with the nucleotide sequence as shown in SEQ ID NO: 2, 4 or 22 and encoding a protein that reduces a double bond between C24 and C25 of the steroid skeleton; and
   (c) DNA encoding a protein consisting of the amino acid sequence as shown in SEQ ID NO:1, 3 or 21.

2. The method according to claim 1, wherein the plant belonging to the family Solanaceae is a potato.

3. The method according to claim 1, wherein the gene expression is suppressed by genetic engineering.

4. The method according to claim 1, wherein the gene expression is suppressed by deletion of a gene that encodes the enzyme.

5. The method according to claim 1, wherein the gene expression is suppressed by crossing involving the use of a plant in which the gene has a mutation and/or polymorphism as a mother plant, and further comprising selecting a progeny obtained by the crossing which has a mutation and/or polymorphism in the gene.

6. The method according to claim 5, wherein the mother plant is obtained by artificial modification of the gene via mutation.

7. The method according to claim 5, wherein the mother plant is obtained and the progeny is selected by steps of:
   (a) isolating a nucleic acid, which is genomic DNA or RNA, from a plant;
   (b) synthesizing cDNA by reverse transcription when the nucleic acid of (i) is RNA;
   (c) amplifying a gene fragment comprising at least a part of the nucleotide sequence as shown in SEQ ID NO: 2, 4, 7, or 22 from DNA obtained in the step (a) or (b);
   (d) determining the presence of a mutation and/or polymorphism in DNA; and
   (e) selecting a plant with reduced glycoalkaloid content by a step of analyzing glycoalkaloid in the plant from (d).

8. A plant belonging to the family Solanaceae which has no traits of dwarfism and a reduced risk for accumulation of glycoalkaloids in which the expression of a gene encoding an enzyme that reduces a double bond between C24 and C25 of the steroid skeleton is suppressed by an artificial procedure, the gene consisting of any one of the DNAs (a) to (c) below:
- (a) DNA consisting of the nucleotide sequence as shown in SEQ ID NO: 2, 4 or 22;
- (b) DNA consisting of a nucleotide sequence having 95% or higher sequence identity with the nucleotide sequence as shown in SEQ ID NO: 2, 4 or 22 and encoding a protein that reduces a double bond between C24 and C25 of the steroid skeleton; and
- (c) DNA encoding a protein consisting of the amino acid sequence as shown in SEQ ID NO:1, 3 or 21.

* * * * *